United States Patent
Wu et al.

(10) Patent No.: US 11,166,953 B2
(45) Date of Patent: Nov. 9, 2021

(54) COMPOUNDS, COMPOSITIONS AND METHODS OF TREATING OR PREVENTING ACUTE LUNG INJURY

(71) Applicant: Yale University, New Haven, CT (US)

(72) Inventors: Dianqing Wu, Cheshire, CT (US); Qianying Yuan, New Haven, CT (US); Abdul Basit, Cincinnati, OH (US); Wenwen Tang, North Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 85 days.

(21) Appl. No.: 16/605,371

(22) PCT Filed: Apr. 17, 2018

(86) PCT No.: PCT/US2018/027980
§ 371 (c)(1),
(2) Date: Oct. 15, 2019

(87) PCT Pub. No.: WO2018/195084
PCT Pub. Date: Oct. 25, 2018

(65) Prior Publication Data
US 2021/0121459 A1 Apr. 29, 2021

Related U.S. Application Data

(60) Provisional application No. 62/486,232, filed on Apr. 17, 2017.

(51) Int. Cl.
*A61K 31/506* (2006.01)
*A61K 45/06* (2006.01)
*A61K 9/00* (2006.01)
*A61P 11/00* (2006.01)

(52) U.S. Cl.
CPC ........ *A61K 31/506* (2013.01); *A61K 9/0043* (2013.01); *A61K 9/0073* (2013.01); *A61K 45/06* (2013.01); *A61P 11/00* (2018.01)

(58) Field of Classification Search
CPC .. A61K 31/506; A61K 9/0073; A61K 9/0078; A61M 11/04; A61M 15/00
See application file for complete search history.

(56) References Cited

U.S. PATENT DOCUMENTS

| | | | |
|---|---|---|---|
| 7,105,530 B2 | 9/2006 | Boloor et al. | |
| 2010/0003199 A1 | 1/2010 | Kilpatrick et al. | |
| 2011/0142837 A1* | 6/2011 | Lambris | A61K 45/06 424/135.1 |
| 2011/0158983 A1 | 6/2011 | Bascomb et al. | |
| 2012/0219522 A1 | 8/2012 | Xi | |
| 2013/0289014 A1* | 10/2013 | Solca | A61K 31/496 514/210.18 |
| 2015/0044288 A1 | 2/2015 | Surber | |
| 2016/0175436 A1 | 6/2016 | Bascomb et al. | |
| 2016/0208002 A1* | 7/2016 | Gomer | A61K 31/496 |

FOREIGN PATENT DOCUMENTS

| | | |
|---|---|---|
| EP | 1343782 B1 | 5/2009 |
| EP | 2311825 A1 | 4/2011 |
| WO | 2015111947 A1 | 7/2015 |

OTHER PUBLICATIONS

McMilan et al., Siglec-E Promotes B2-Integrin-dependent NADPH Oxidase Activation to Suppress Neutrophil Recruitment to the Lung, J. of Bio. Chem., vol. 289, No. 29, p. 20370-20376 (2014). (Year: 2014).*
Kapadia, et al., Risk of Liver Toxicity with the Angiogenesis Inhibitor Pazopanib in Cancer Patients, Acta Oncologica, 52: 1202-1212 (2013). (Year: 2013).*
Extended European Search Report for European Patent Application No. 18787714.7 dated Dec. 22, 2020.
CAS RN 444731-52-6. PubChem Compound Summary Pazopanib. PubChem CID: 1011397. Create Date: Oct. 25, 2006; Accessed Aug. 23, 2020.
CAS RN 635702-64-6, PubChem Summary Pazopanib hydrochloride. PubChem CID: 11525740. Create Date: Oct. 26, 2006. Accessed Aug. 23, 2020.
International Search Report and Written Opinion for PCT International Application No. PCT/US2018/027980 dated Jun. 29, 2018.
Votrient (pazopanib) tablets Label, GlaxoSmithKline, 2009, 1-18.
Ahmad , et al., "Development and Validation of a High-Throughput Intrinsic ATPase Activity Assay for the Discovery of MEKK2 Inhibitors", J Biomol Screen. 18(4), Apr. 2013, 388-399.
Basit , et al., "Loss of MEKK2 and MEKK3 Results in Increased ROS and is Protective in LPS-Induced Lung Injury", The Society for Leukocyte Biology's 49th Annual Meeting and "Neutrophil 2016" Verona, Italy, 2016.
Brown , et al., "MAP kinase kinase kinase-2 (MEKK2) regulates hypertrophic remodeling of the right ventricle in hypoxia-induced pulmonary hypertension", Am J Physiol Heart Circ Physiol. 304(2), Jan. 2013, H269-281.
Gan , et al., "PRR5L degradation promotes MTORC2-mediated PKCδphosphorylation and cell migration downstream of Gα12", Nat Cell Biol. 14(7), May 2012, 686-696.
Kapadia , et al., "Risk of liver toxicity with the angiogenesis inhibitor pazopanib in cancer patients", Acta Oncol. 52(6), Aug. 2013, 1202-1212.
Kim , et al., "MEKK3 is essential for lipopolysaccharide-induced interleukin-6 and granulocyte-macrophage colony-stimulating factor production in macrophages", Immunology. 120(2), Feb. 2007, 242-250.
McMillan , et al., "Siglec-E promotes β-integrin-dependent NADPH oxidase activation to suppress neutrophil recruitment to the lung", J Biol Chem. 289(29), Jul. 2014, 20370-20376.

(Continued)

*Primary Examiner* — Erich A Leeser
(74) *Attorney, Agent, or Firm* — Saul Ewing Arnstein & Lehr LLP; Kathryn Doyle; Domingos J. Silva

(57) ABSTRACT

The invention includes methods of preventing or treating acute lung injury using a MAP3K2/MAP3K3 inhibitor. The invention further comprises compositions, and kits comprising compositions useful within the invention.

15 Claims, 30 Drawing Sheets

(56) References Cited

OTHER PUBLICATIONS

Mongan, et al., "Mitogen-activated protein kinase kinase kinase 1 protects against nickel-induced acute lung injury", Toxicol Sci. 104(2), May 2008, 405-411.

Obenauer, et al., "Scansite 2.0: Proteome-wide prediction of cell signaling interactions using short sequence motifs", Nucleic Acids Res. 31(13), Jul. 2003, 3635-3641.

* cited by examiner

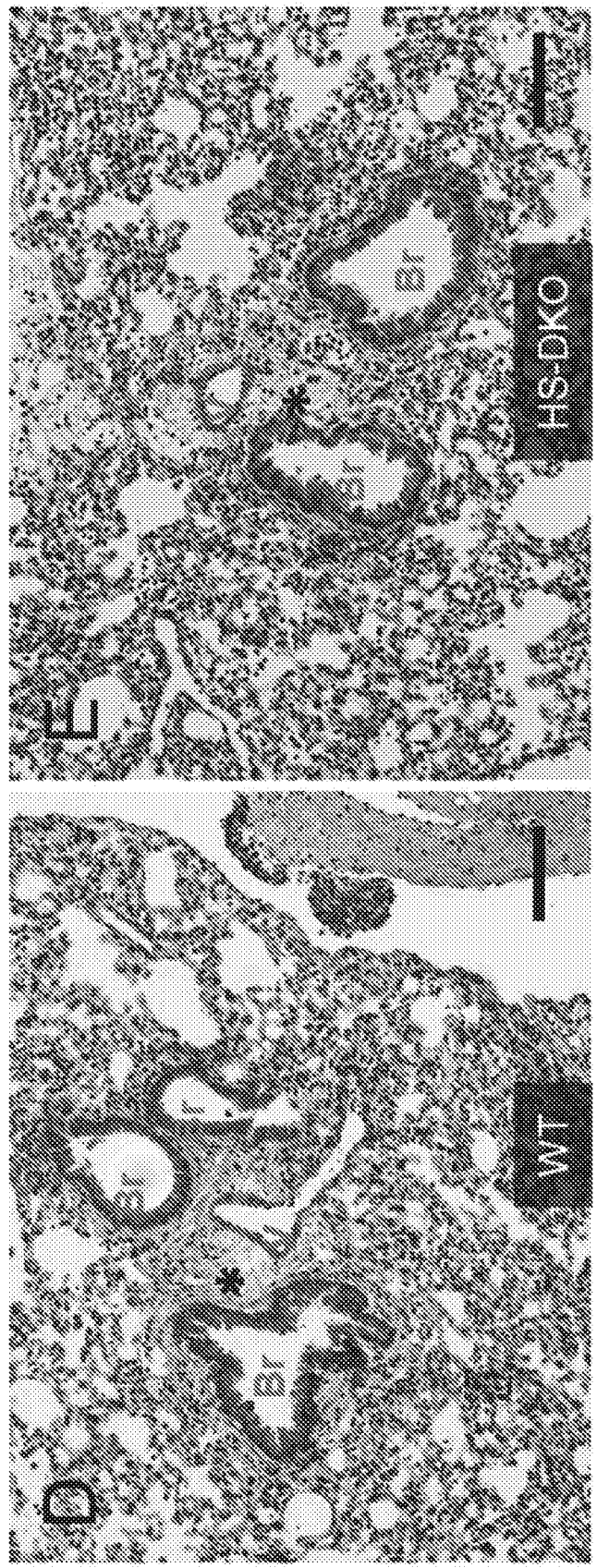

0.43" = 50 μm

FIG. 12A FIG. 12B FIG. 12C ns, and a PBl domain near the N terminus. The kinase domains
COMPOUNDS, COMPOSITIONS AND METHODS OF TREATING OR PREVENTING ACUTE LUNG INJURY

CROSS-REFERENCE TO RELATED APPLICATIONS

This application is a 35 U.S.C. § 371 national phase application from, and claims priority to, International Application No. PCT/US2018/027980, filed Apr. 17, 2018, and published under PCT Article 21(2) in English, which claims priority under 35 U.S.C. § 119(e) to U.S. Provisional Application No. 62/486,232, filed Apr. 17, 2017, all of which applications are incorporated herein by reference in their entireties.

STATEMENT REGARDING FEDERALLY SPONSORED RESEARCH OR DEVELOPMENT

This invention was made with government support under HL135805 awarded by National Institutes of Health. The government has certain rights in the invention.

BACKGROUND OF THE INVENTION

The incidence of acute lung injury (ALI) and its more severe form, acute respiratory distress syndrome (ARDS), is reported to be around 200,000 per year in the US with a mortality rate of around 40%. The diseases are the manifestations of an inflammatory response of the lung to direct or indirect insults, and are characterized by severe hypoxemia and a substantial reduction in pulmonary compliance due to diffuse alveolar damage, neutrophilic inflammation, and protein-rich edema in the lungs. Care of these conditions is largely dependent on supportive measures. There is currently a lack of effective pharmacological interventions. Pharmacological therapies that have been tested in patients with ALI/ARDS failed to reduce mortality. There is thus a clear unmet medical need for therapeutic intervention of this disease.

One of the hallmarks of ALI is abundant presence of neutrophils in the lungs. Neutrophils are the most abundant leukocytes in human circulation, playing important roles in innate immunity against microbial infections and also contributing to inflammation-related tissue damages. During the inflammation, neutrophils are recruited to the sites of injury and infection from circulation through a multi-step process, which includes rolling and firm adhesion on endothelial cells, intravascular crawling, diapedesis, and extravascular chemotaxis. Once at the sites, neutrophils perform a number of tasks including phagocytosis, release of preformed granule enzymes, and production of reactive oxygen species (ROS). Evidence has clearly linked neutrophils to the pathogenesis of ALI/ARDS. Although crossing of the alveolar epithelium by neutrophils does not directly cause an increase in lung epithelial permeability, neutrophils play important roles in pulmonary edema with the underlying mechanisms that remain incompletely understood.

While neutrophil extracellular traps and granule enzymes such as neutrophil elastase contribute to the pathology of ALI, including lung edema, any role of ROS in ALI/ARDS is still debatable. Neutrophils produce ROS primarily through the phagocyte NADPH oxidase, which is a member of the NOX family. It consists of four cytosolic components ($p47^{phox}$, $p67^{phox}$, $p40^{phox}$, and Rac) and two membrane subunits ($gp91^{phox}$/NOX2 and $p22^{phox}$). When the cells are activated by stimuli such as chemo-attractants, the cytosolic components are recruited to the membrane components to form the active holoenzyme to produce ROS. One of the key activation events is the phosphorylation of the cytosolic $p47^{phox}$ subunit by protein kinases including PKC. The phosphorylation disrupts auto-inhibitory intramolecular interaction involving the internal SH3 domains, leading to its interaction with $p22^{phox}$, required for the activation of the NADPH oxidase.

MAP3K2 and MAP3K3 are two highly conserved members of the MEK kinase (MEKK) subgroup of the MAP3K superfamily. They contain a kinase domain in the C terminus and a PB1 domain near the N terminus. The kinase domains of MAP3K2 and MAP3K3 share 94% sequence identity, and these two kinases are expected to share substrates. Transient expression of the kinases in vitro leads to their auto-activation and activation of ERK1 and ERK2, p38, JNK, and ERK5. In mice, these kinases are involved in cardiovascular development, lymphocyte differentiation and NF-kappaB regulation. However, their roles in primary myeloid cell biology or ALI have not been investigated.

There is a need in the art to identify novel therapeutic treatments that can be used to treat or prevent ALI/ARDS in patients afflicted with those diseases. The present invention addresses and meets this need.

BRIEF SUMMARY OF THE INVENTION

The invention provides a method of treating or preventing acute lung injury (ALI) in a subject in need thereof. The invention further provides a method of treating or preventing lung fibrosis in a subject in need thereof. The invention further comprises a kit comprising a compound or composition useful within the methods of the invention.

In certain embodiments, the method comprises administering to the subject a therapeutically effective amount of pazopanib, or a salt or solvate thereof. In other embodiments, the administration route is oral. In other embodiments, the administration route is parenteral. In yet other embodiments, the administration route is nasal. In yet other embodiments, the administration route is inhalational. In yet other embodiments, the administration route is intratracheal. In yet other embodiments, the administration route is intrapulmonary. In yet other embodiments, the administration route is intrabronchial. In yet other embodiments, the administration route is selected from the group consisting of oral, parenteral, nasal, inhalational, intratracheal, intrapulmonary, and intrabronchial. In yet other embodiments, the administration route is selected from the group consisting of nasal, inhalational, intratracheal, intrapulmonary, and intrabronchial. In yet other embodiments, the administration is done using a nebulizer.

In certain embodiments, the subject is in an intensive care unit (ICU) or emergency room (ER). In other embodiments, the acute lung injury is acute respiratory distress syndrome (ARDS).

In certain embodiments, the subject is further administered at least one additional agent and/or therapy that treats, prevents or reduces the symptoms of the acute lung injury. In other embodiments, the subject is further administered at least one additional agent and/or therapy that treats, prevents or reduces the symptoms of the lung fibrosis.

In certain embodiments, the pazopanib, or a salt or solvate thereof, is administered to the subject at a frequency selected from the group consisting of about three times a day, about twice a day, about once a day, about every other day, about every third day, about every fourth day, about every fifth day, about every sixth day and about once a week. In other embodiments, the pazopanib, or a salt or solvate thereof, is formulated as a dry powder blend.

In certain embodiments, administration of the pazopanib, or a salt or solvate thereof, to the subject does not cause at least one significant adverse reaction, side effect and/or toxicity associated with oral/systemic administration of the pazopanib, or a salt or solvate thereof, to a subject suffering from cancer. In other embodiments, the at least one adverse reaction, side effect and/or toxicity is selected from the group consisting of hepatotoxicity, prolonged QT intervals and torsades de pointes, hemorrhagic event, decrease or hampering of coagulation, arterial thrombotic event, gastrointestinal perforation or fistula, hypertension, hypothyroidism, proteinuria, diarrhea, hair color changes, nausea, anorexia, and vomiting.

In certain embodiments, the subject is dosed with an amount of pazopanib, or a salt or solvate thereof, that is lower than the amount of pazopanib, or a salt or solvate thereof, with which a subject suffering from cancer is dosed orally/systemically for cancer treatment.

In certain embodiments, the subject is a mammal. In other embodiments, the mammal is a human.

In certain embodiments, the kit comprises pazopanib, or a salt or solvate thereof. In other embodiments, the kit comprises an applicator. In yet other embodiments, the kit comprises an instructional material for use thereof. In yet other embodiments, the kit comprises at least one additional agent that treats, prevents or reduces the symptoms of the acute lung injury and/or lung fibrosis. In yet other embodiments, the instructional material comprises instructions for treating or preventing acute lung injury and/or lung fibrosis in a subject.

The invention further provides a method of evaluating efficacy of a drug in treating ALI. In certain embodiments, the method comprises contacting a neutrophil with the drug and measuring neutrophil ROS production levels after the contacting. In other embodiments, if the neutrophil ROS production levels increase after the contacting, the drug is efficacious in treating ALI.

The invention further provides a method of evaluating efficacy of a drug in treating a subject suffering from ALI. In certain embodiments, the method comprises measuring neutrophil ROS production levels in the subject after being administered the drug. In other embodiments, if the neutrophil ROS production levels in the subject after being administered the drug are higher than the neutrophil ROS production levels in the subject before being administered the drug, the drug is efficacious in treating ALI in the subject.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A illustrates loss of MAP3K2 and 3 proteins in HS-DKO neutrophils. FIG. 1B illustrates reduced pulmonary permeability in HS-DKO mice. HS-DKO and control WT mice were treated with LPS via intranasal route. Lung permeability to FITC-labeled albumin was determined by measuring the fluorescence of BAL 24 hours after injury induction. FIG. 1F illustrates reduced pulmonary permeability in HS-DKO mice. HS-DKO and control WT mice were treated with HCl via oral-tracheal intubation. Lung permeability to FITC-labeled albumin was determined by measuring the fluorescence of BAL 6 hours after injury induction. Data are presented as mean±sem (Student t-Test, *$p<0.05$, n=8). FIGS. 1C-1D & 1G illustrate representative histology of lung samples from FIG. 1B and FIG. 1F, respectively. Br, bronchus; V, blood vessel; *, edema. FIG. 1E illustrates HS-DKO mice show extended survival by LPS-induced lung injury, and FIG. 1H illustrates HS-DKO mice show extended survival by HCl-induced lung injury. The mice were treated as in FIG. 1B and FIG. 1F, and observed for survival (the Mantel-Cox Log-Rank test).

FIGS. 2A-2D illustrate the finding that MAP3K2/3-null neutrophil show normal chemotaxis. Representative cell migration traces from a Dunn chamber chemotaxis assay are shown in FIGS. 2A-2B. The translocation and directionality parameters for how fast the cells move and how well they follow the chemoattractant gradient are shown in FIGS. 2C-2D. n=50. FIG. 2E illustrates adhesion of neutrophils to endothelial cells under shear flow. n=3. FIGS. 2F-2G illustrate cell surface expression of LFA-1 and MAC-1 integrins on neutrophils. n=3. FIG. 2H illustrates binding of neutrophils to ICAM-1, which reflects the avidity of integrins on neutrophil upon activation. n=3. FIG. 2I illustrates infiltration of neutrophils into inflamed peritonea. n=5. FIGS. 2J-2K illustrates release of MMP and MPO from neutrophil granules upon stimulation. n=3.

FIGS. 3A-3E illustrate the finding that MAP3K2/3 inhibits ROS release from neutrophils dependently of kinase activity. FIG. 3A illustrates the finding that loss of MAP3K2/3 increases ROS release from neutrophils. Representative ROS measurement traces are shown in the left panel, whereas ROS amounts calculated from the areas under the traces from more than five mice are summarized in the right panel (data are presented as mean±sem, Student t-Test, *$p<0.05$, n=3). The experiments were repeated at least 3 times. FIG. 3B illustrates the finding that expression of WT MAP3K3, but not its kinase dead mutant, suppresses ROS production in DKO neutrophils. Neutrophils were transiently transfected with plasmids for GFP, MAK3K3-GFP, MAP3K3 kinase dead (KD) or PB1 domain-deletion mutant fused with GFP. GFP-positive cells were sorted the next day and used for ROS release assay. The expression of MAP3K3 and its mutants were detected by Western analysis. Data are presented as mean±sem (Student t-Test, *$p<0.05$, n=3). FIGS. 3C-3E illustrate the finding that superoxide scavenger BHA abrogates the difference between HS-DKO and control WT mice in LPS-induced lung injury. Mice under diet containing BHA were subjected to LPS-induced lung injury. n=5.

FIG. 4A illustrates the finding that MAP3K3 phosphorylates p47phox. In vitro kinase assay was performed using recombinant MAPK3K3 and NADPH oxidase subunits immunoprecipitated from HEK293 cells. The NADPH oxidase subunits were transiently expressed with an HA-tag, and anti-HA antibody was used for immunoprecipitation. FIG. 4B illustrates the finding that MAP3K3 phosphorylates S208 of p47phox. In vitro kinase assay was performed using recombinant MAP3K3 and GST-fused fragment (p47SH3) of wild type (WT) or S208E mutated (SE) p47phox (residues 151-286) that contains the two SH3 domains. The quantification of the phosphorylation was done by a phosphoimager. FIG. 4C illustrates the finding that phosphomimetic mutation of Ser-208 of p47phox leads to reduced activity in the reconstituted ROS production assay. COS-7 cells were cotransfected with plasmids for p22phox, p67phox, and p97phox together with WT p47phox or its S208A (SA) or S208E (SE) mutant. The PMA-induced ROS production are shown. Data are presented as mean±sem (Student t-Test, *p<0.05, n=5). FIG. 4D illustrates the finding that WT p47phox, but not its S208A mutant, is inhibited by MAP3K3. COS-7 cells were cotransfected with plasmids for p22phox, p67phox, and p97phox together with WT p47phox (left panel) or its S208A (right panel) mutant in the presence or absence of MAP3K3. The PMA-induced ROS production are shown. Data are presented as mean±sem (Student t-Test, *p<0.05, n=5). FIG. 4E illustrates the finding that phosphomimetic mutation of Ser-208 of p47phox impairs the interaction with p22phox. GST pull-down assay was performed with recombinant GST-p47SH3 carrying a substitution of Ala or Glu for Ser-208 and MBP-fused C-terminus (residues 96-164) of p22phox (p22C). Western analysis was used for detection of the proteins. FIG. 4F illustrates the finding that phosphorylation of Ser-208 of p47phox is stimulated by fMLP. Neutrophils were stimulated with fMLP (1 µM) for varying durations, followed by Western analysis. FIG. 4G illustrates the finding that FMLP-stimulated p47phox phosphorylation depends on MAP3K2/3.

FIG. 5A illustrates the finding that pazopanib inhibits phosphorylation of Ser-208 of p47phox. Neutrophils were pretreated with pazopanib (pazo) for 10 min before stimulation by fMLP (1 µM), followed by Western analysis. FIGS. 5B-5C illustrate the finding that pazopanib increases ROS release from neutrophils depending on MAP3K2/3. Neutrophils were pretreated with pazopanib (20 nM in FIG. 5C) for 10 min before stimulation by fMLP (1 µM) and ROS measurement. Data are presented as mean±sem (Student t-Test, *p<0.05, n=3). FIGS. 5D-5E illustrate the finding that pazopanib treatment attenuates LPS-induced lung injury. Mice (C57Bl female) were treated with 60 mg/Kg/day pazopanib via gavage two day before lung injury induction by LPS. One day after lung injury induction, lung permeability (FIG. 5D) and histology (FIG. 5E) were examined. The experiment was repeated twice with similar outcomes. Data from one experiment are presented as mean±sem (Student t-Test, *p<0.05, n=5). FIG. 5F illustrates the finding that pazopanib treatment reduces mortality of mice with LPS-induced lung injury. The C57B1 mice were treated as above and their survival was analyzed by the Mantel-Cox Log-Rank test.

FIG. 7A illustrate a non-limiting model that describes how MAP3K2/3 inhibition leads to the increase in ROS production from neutrophils and AKT hyperactivation in endothelial cells as well as pericytes. Without wishing to be limited by any theory, hyperactivation of AKT leads to improved vascular integrity and reduced permeability, thus the healthier lungs during ALI. FIGS. 7B-7C illustrate the finding that co-culture of MAP3K2/3-deficienct neutrophils (DKO) causes greater AKT phosphorylation compared to that of WT neutrophils, and this difference in AKT phosphorylation is abrogated by the presence of catalase (Cat), but not superoxide dismutase (SOD). FIG. 7D illustrates TEER measurement of mouse lung endothelial cells co-cultured with WT or DKO neutrophils in the presence or absence of SOD. The arrow indicates the time point at which neutrophils were added.

FIG. 8A illustrate a validation of LPS-induced lung injury model. Mice were treated with LPS via intranasal route. Lung permeability to FITC-labeled albumin was determined by measuring the fluorescence in BALF 24 hours after injury induction. Data are presented as mean±sem (Student t-Test, n=4). n=5. FIGS. 8B-8E illustrate how whole lung from mice described in FIGS. 1A-1E were analyzed by flow cytometry (FIGS. 8A-8D) and by ELISA (FIG. 8E).

FIG. 8F illustrates a schematic of HCl-induced lung injury model. FIGS. 8H-8J illustrate how whole lung were analyzed by flow cytometry (FIGS. 8G-8I) and by ELISA (FIG. 8J).

FIGS. 10A-10B: COS-7 cells were transfected with plasmids for NANPH oxidase subunits as indicated in the figures and treated with and without PMA. ROS production and protein expression were determined. FIG. 10C illustrates the finding that WT MAP3K3, but not its kinase dead mutant, can inhibit ROS production in the reconstituted COS-7 system. FIG. 10D illustrates a non-limiting schematic model that depicts how MAP3K2/3 suppresses ROS production.

FIGS. 12A-12K illustrate the finding that LPS induced lung injury by increasing pulmonary permeability. FIGS.

12A-12B illustrate the finding that pazopanib inhibits MEKK3 and increases ROS production from human neutrophils. Human neutrophils were stimulated with fMLP (100 nM) in the presence and absence of 20 nM pazopanib. Data in FIG. 12B are presented as mean±sem (*, P<0.05, student t-test; n=5). FIGS. 12C-12D illustrate the finding that BHA abrogates pazopanib's effect on lung permeability. HS-DKO Mice were fed on regular chew or chew containing BHA and treated with 60 mg/Kg/day pazopanib via gavage starting two days before lung injury induction by LPS. One day after lung injury induction, lung permeability was determined. Data in FIG. 12C are presented as mean±sem (n=5). Representative histology is shown in FIG. 12D. FIG. 12E illustrates the finding that therapeutic treatment of pazopanib reduces mortality of mice with LPS-induced lung injury. Mice (C57B1 female, 8 weeks) were treated with 1.5 mg/Kg pazopanib via intra-nasal 24 h after lung injury induction by LPS (80 μg/g, 32 mg/ml) and their survival was analyzed by the Mantel-Cox Log-Rank test. FIGS. 12F-12G illustrates the finding that pazopanib treatment attenuates HCl-induced lung injury. Mice (C57B1 female, 8 weeks) were treated with 1.5 mg/Kg pazopanib via intra-nasal 1 h after lung injury induction by HCl (0.05 M, 2.5 μl/g). Six hours after lung injury induction, lung permeability (FIG. 12D) and histology (FIG. 12E) were examined. The experiment was repeated twice with similar outcomes. Data from one experiment are presented as mean±sem (Student t-Test, *p<0.05, n=5). FIG. 12H illustrates the finding that pazopanib treatment reduces mortality of mice with LPS-induced lung injury. Mice (C57B1 female, 8 weeks) were treated with 2.5 mg/Kg pazopanib via intra-nasal 1 h after lung injury induction by HCl (0.1 M, 2.5 μl/g) and their survival was analyzed by the Mantel-Cox Log-Rank test. FIG. 12I-12K illustrates the finding that preventative treatment of pazopanib reduces lung permeability and mortality of mice with HCl-induced lung injury. FIG. 12J illustrates the finding that pazopanib pretreatment attenuates HCl-induced lung injury. Mice (C57B1 female, 8 weeks) were treated with 1.5 mg/Kg pazopanib via intra-nasal 0.5 hour before lung injury induction by HCl (0.05 M, 2.5 μl/g). Six hours after lung injury induction, lung permeability were examined. The experiment was repeated twice with similar outcomes. Data from one experiment are presented as mean±sem (Student t-Test, *p<0.05, n=5). FIG. 12K illustrates the finding that pazopanib pretreatment reduces mortality of mice with HCl-induced lung injury. Mice (C57B1 female, 8 weeks) were treated with 1.5 mg/Kg pazopanib via intra-nasal 0.5 hour before lung injury induction by HCl (0.1 M, 2.5 μl/g) and their survival was analyzed by the Mantel-Cox Log-Rank test.

FIG. 13A illustrates increases in phosphorylation of AKT at S473 in the protein extracts from LPS-induced lungs of HS-DKO mice. FIGS. 13B-13C illustrate supplementary images of CD31 and SMA staining alone of LPS-inured lung sections for FIG. 6, Panels A-D. FIGS. 13D-13E illustrate an effect of pazopanib on AKT phosphorylation in lung samples from WT and HS-DKO mice. FIG. 13F illustrates the finding that AKT-inhibitor MK-2206 abrogates the effect of pazopanib on permeability in LPS-injured lungs. Mice were treated with MK-2206 (10 mg/Kg) in the presence or absence of 60 mg/Kg/day pazopanib via gavage starting two days before lung injury induction by LPS. n=5.

FIGS. 14A and 14B illustrates Rac1 activation in the protein extracts from H2O2-induced mouse lung endothelial cells (MLEC). FIGS. 14C-14D illustrates Rac1 activation in MLEC which were co-cultured with fMLP induced MAP3K2/3 deficient neutrophils.

FIGS. 16A and 16D illustrate treatment results for WT and p47-HKO mice. FIGS. 16B-16C illustrate the effect of pazopanib on permeability, whereas FIGS. 16D-16E illustrate beneficial effects of pazopanib on survival. FIGS. 16A, 16B and 16D illustrate the finding that loss of p47$^{phox}$, a key element for ROS generation, exacerbate lung permeability (FIGS. 16A-16B) and decrease survival rate (FIG. 16D) in HCl-induced lung injury. Loss of p47$^{phox}$ abrogated the therapeutic effect of pazopanib indicated by HCl-induced lung permeability (FIG. 16C) and survival rate (FIG. 16E).

DETAILED DESCRIPTION OF THE INVENTION

The present invention relates in part to the unexpected discovery that increased reactive oxygen species (ROS) production from neutrophils by MAP3K2 and/or MAP3K3 inhibition protects lung during acute injury. ROS is generally believed to exacerbate tissue injuries. However, as demonstrated herein, moderate elevation of NADPH oxidase-derived ROS in neutrophils ameliorates acute lung injury (ALI) manifestations and reduces mortality in mice. MAP3K2 and MAP3K3 were herein identified as being novel negative regulators of neutrophil NADPH oxidase by phosphorylating p47$^{phox}$ at Serine 208. Neutrophils lacking MAP3K3 and its homolog MAP3K2 produce a greater amount of ROS, while showing normal chemotaxis, adhesion to endothelial cells, infiltration, and degranulation. Genetic loss of MAP3K3 in myeloid cells and MAP3K2 in hematopoietic cells was found to protect mice from pulmonary edema and mortality in a mouse ALI model, accompanied by enhanced AKT activation in the lung vasculature. These phenotypes can be recapitulated by a MAP3K2/3 inhibitor pazopanib.

Thus, these present study sheds new light on the role of ROS in ALI and reveals a previously unknown mechanism for regulation of ROS production. Further, it provides a potential target and agent for therapeutic intervention of ALI, a life-threatening disease that currently lacks pharmacological treatment. In a non-limiting aspect, these results support the therapeutic potential of aerosolized administration of pazopanib to subjects suffering from ALI. In certain embodiments, targeted administration of pazopanib within injured lung attenuate or completely resolve ALI, for example by treating, reversing or ameliorating diffuse alveolar damage and/or edema.

The present invention provides a method of treating or preventing lung fibrosis and/or acute lung injury in a subject, comprising administering to the subject a therapeutically effective amount of pazopanib or a salt or solvate thereof. In certain embodiments, the pazopanib, or salt or solvate thereof, is directly delivered into the lung using an inhaler, for example. This allows for effective delivery of an optimal drug dose within areas of affected lung, maximizing its therapeutic effects and minimizing potential side effects arising from systemic administration. In certain embodiments, localized delivery of pazopanib minimizes any possible side effects of increase in ROS production in non-lung tissues.

Figure 10A:
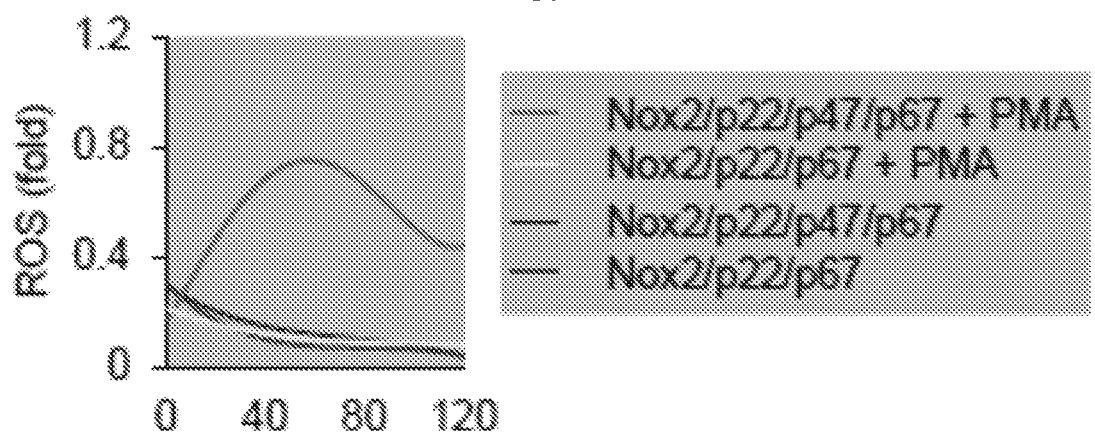
FIGS. 10A-10D illustrate validation of the reconstituted ROS production system in COS-7 cells.
Figure 10B:
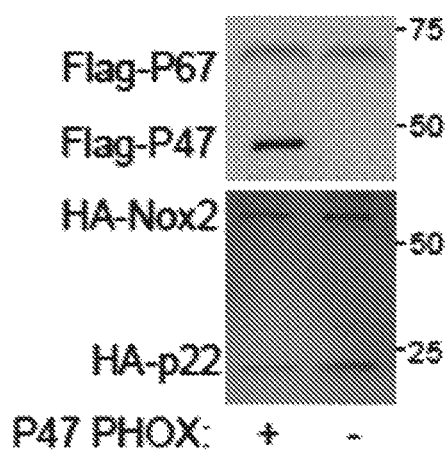
Figure 10C:
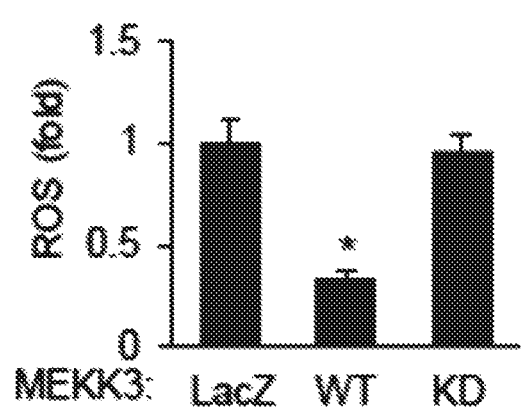
Figure 10D:
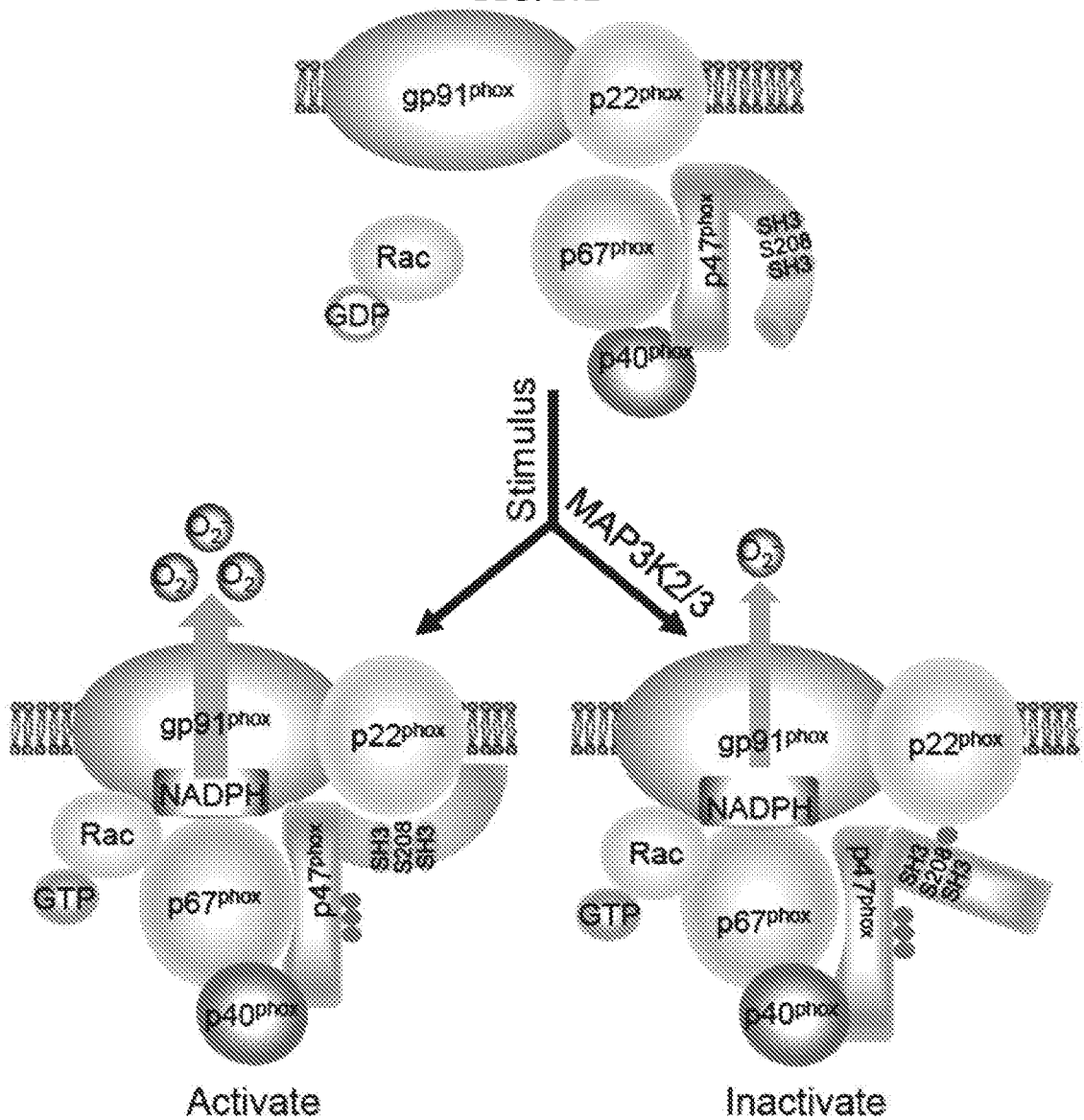
Figure 11:
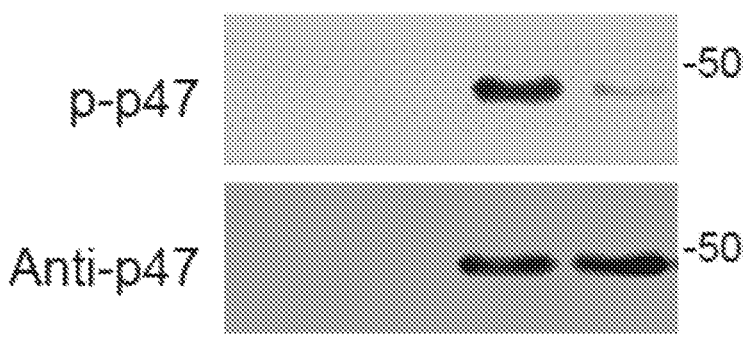
FIG. 11 illustrates validation of anti-phospho-S208 $p47^{phox}$ antibody. HEK293 cells were cotransfected with WT or kinase dead MAP3K3 together with WT or S208A $p47^{phox}$. Western analysis was performed the next day.
Figure 11:
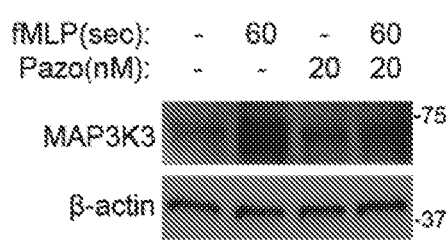
Figure 11:
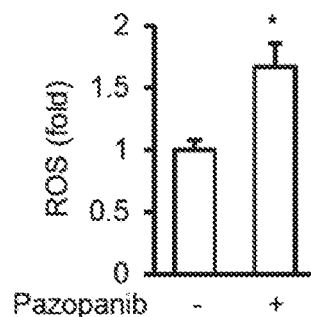
Figure 11:
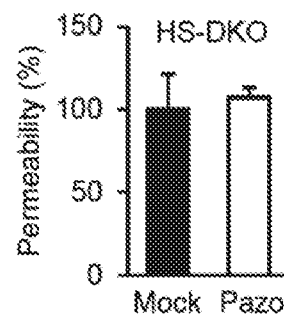

As discussed herein, a previously unknown function for protein kinases MAP3K2 and 3 in negative regulation of phagocytic NADPH oxidase was identified. These kinases phosphorylate Ser-208 of $p47^{phox}$. This phosphorylation, in contrast to previously known phosphorylation sites in $p47^{phox}$, prevents $p47^{phox}$ interaction with $p22^{phox}$ and leads to inhibition of the NADPH oxidase activity (FIG. 10D). As expected, either the genetic loss of MAP3K2/3 or their pharmacological inhibition resulted in increased ROS production. The increased ROS protected mice from LPS induced ALI.

The present results indicate that pharmacological induction of increased ROS can be protective in a disease model. Most of the attention has been given to the detrimental effects of ROS, as excessive amounts of ROS can cause damage to lipids, proteins, and DNA. At the time of the invention it was unknown whether an increase in ROS production would be effective in curbing inflammatory responses and provide beneficial therapeutic effects, in particular in a clinically practical manner. The present studies demonstrate that genetic or pharmacological inhibition of MAP3K2 and MAP3K3 leads to increases in ROS production in neutrophils and attenuates lung injury in mice, the latter of which depends on ROS. Pazopanib, an FDA-approved small molecular drug, which inhibits MAP3K2/3, elevates ROS in both human and mouse neutrophils and alleviates lung injury phenotypes in mice, provides a clinically feasible way to achieve the therapeutic benefits. Without wishing to be limited by any theory, once it being released outside cells, ROS can be converted to $H_2O_2$ as superoxide dismutase (SOD) is abundantly present in lung tissues, and $H_2O_2$ has at moderate levels a protective role in pulmonary vasculatures integrity, leading to reduction in permeability and edema during injury. In certain non-limiting embodiments, increased ROS generation either with the genetic loss of MAP3K2/3 or with their pharmacologic inhibition by pazopanib represents an optimal situation where ROS was sufficient to activate protective AKT phosphorylation but not high enough to cause irreversible damage. In certain embodiments, increased ROS production in neutrophils can be used as a readout for efficacy of drugs being used to treat ALI in a subject Definitions Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the phrase "acute lung injury" or "ALI" refers to a syndrome consisting of acute hypoxemic respiratory failure with bilateral pulmonary infiltrates, which is associated with both pulmonary and nonpulmonary risk factors and that is not primarily due to left atrial hypertension.

As used herein, the phrase "acute respiratory distress syndrome" or "ARDS" refers to a subtype of acute lung injury characterized by more severe hypoxemia.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound of the invention or salt thereof along with a compound that may also treat the disorders or diseases contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pazopanib" refers to 5-((4-((2,3-dimethyl-2H-indazol-6-yl)(methyl)amino)pyrimidin-2-yl)amino)-2-methylbenzenesulfonamide, or a salt and/or solvate thereof:

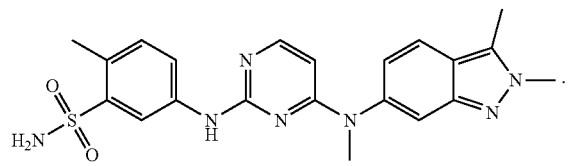 [SMILES: Cc1ccc(Nc2nccc(N(C)c3ccc4c(C)n(C)nc4c3)n2)cc1S(N)(=O)=O]

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "prevent," "preventing" or "prevention," as used herein, means avoiding or delaying the onset of symptoms associated with a disease or condition in a subject that has not developed such symptoms at the time the administering of an agent or compound commences.

As used herein, the term "ROS" refers to reactive oxygen species. Non-limiting examples of ROS are peroxide, superoxide, hydroxyl radical, and singlet oxygen.

The term "salt" embraces addition salts of free acids and/or basis that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds and/or compositions useful within the methods of the invention. Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, 2-hydroxyethanesulfonic, p-toluenesulfonic, trifluoromethanesulfonic, sulfanilic, cyclohexylaminosulfonic, stearic, alginic, β-hydroxybutyric, salicylic, galactaric and galacturonic acid. Suitable pharmaceutically acceptable base addition salts of compounds and/or compositions of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (also known as N-methylglucamine) and procaine. All of these salts may be prepared from the corresponding compound by reacting, for example, the appropriate acid or base with the compound and/or composition.

As used herein, a "solvate" of a compound refers to the entity formed by association of the compound with one or more solvent molecules. Solvates include water, ether (e.g., tetrahydrofuran, methyl tert-butyl ether) or alcohol (e.g., ethanol) solvates, acetates and the like. In certain embodiments, the compounds described herein exist in solvated forms with solvents such as water, and ethanol. In other embodiments, the compounds described herein exist in unsolvated form.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

By the term "specifically bind" or "specifically binds," as used herein, is meant that a first molecule preferentially binds to a second molecule (e.g., a particular receptor or enzyme), but does not necessarily bind only to that second molecule.

The following non-limiting abbreviations are used herein: ALI, acute lung injury; ARDS, acute respiratory distress syndrome; BSA, bovine serum albumin; DMEM, Dulbecco's Modified Eagle Medium; fMLP, N-Formyl-L-methionyl-L-leucyl-L-phenylalanine; MSS, Hanks balanced salt; HRP, horse radish peroxidase; LPS, lipopolysaccharide; MAP3K2 or MEKK2, mitogen-activated protein kinase kinase kinase 2; MAP3K3 or MEKK3, mitogen-activated protein kinase kinase kinase 3; MEK, mitogen-activated protein kinase kinase; MEKK, MEK kinase; PBS, phosphate buffered saline; PFA, paraformaldehyde; PMA, phorbol 12-myristate 13-acetate; RBC, red blood cell; ROS, reactive oxygen species; TG, thioglycolate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds and Compositions

In certain embodiments, pazopanib, or a salt or solvate thereof, is useful within the methods of the invention. In other embodiments, compounds and/or compositions useful within the invention are recited in U.S. Pat. Nos. 7,105,530; 7,262,203; 7,858,626; and 8,114,885; all of which are incorporated herein in their entireties by reference. Compositions comprising pazopanib, or a salt or solvate thereof, are also contemplated within the invention.

Methods

The invention includes a method of preventing or treating acute lung injury in a subject in need thereof. The invention includes a method of preventing or treating lung fibrosis in a subject in need thereof.

In certain embodiments, the method comprises administering to the subject therapeutically effective amounts of pazopanib, or a salt or solvate thereof. In other embodiments, the administration route is oral. In other embodiments, the administration route is parenteral. In yet other embodiments, the administration route is nasal. In yet other embodiments, the administration route is inhalational. In yet other embodiments, the administration route is intratracheal. In yet other embodiments, the administration route is intrapulmonary. In yet other embodiments, the administration route is intrabronchial. In yet other embodiments, the administration route is selected from the group consisting of oral, parenteral, nasal, inhalational, intratracheal, intrapulmonary, and intrabronchial. In yet other embodiments, the administration route is selected from the group consisting of nasal, inhalational, intratracheal, intrapulmonary, and intrabronchial. In yet other embodiments, the administration is done using a nebulizer. In yet other embodiments, the acute lung injury is acute respiratory distress syndrome.

In certain embodiments, the compositions of the invention are administered to the subject about three times a day, about twice a day, about once a day, about every other day, about every third day, about every fourth day, about every fifth day, about every sixth day and/or about once a week.

In certain embodiments, the dose of pazopanib, or a salt or solvate thereof, required to treat acute lung injury in a subject using a route of administration selected from the group consisting of nasal, inhalational, intratracheal, intrapulmonary, intrabronchial, and inhalation, is lower than the dose of pazopanib, or a salt or solvate thereof, required to treat cancer (such as but not limited to advanced renal cell carcinoma) in a subject orally. In other embodiments, the dose used within the methods of the invention is about 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95 or 1:100 that of the oral dose required to treat cancer, in terms of mass of pazopanib, or a salt or solvate thereof, per subject's weight. In yet other embodiments, the dose of drug is about 5-200 mg/day.

In certain embodiments, administration of the compound and/or composition to the subject does not cause significant adverse reactions, side effects and/or toxicities that are associated with systemic administration of the compound and/or composition. Non-limiting examples of adverse reactions, side effects and/or toxicities include, but are not limited to hepatotoxicity (which may be evidenced and/or detected by increases in serum transaminase levels and bilirubin), prolonged QT intervals and torsades de pointes, hemorrhagic events, decrease or hampering of coagulation, arterial thrombotic events, gastrointestinal perforation or fistula, hypertension, hypothyroidism, proteinuria, diarrhea, hair color changes (depigmentation), nausea, anorexia, and vomiting.

In certain embodiments, the subject is undergoing treatment in an intensive care unit (ICU). In other embodiments, the subject is undergoing treatment in an emergency room (ER). In yet other embodiments, the subject is on a ventilator.

In certain embodiments, the subject is further administered at least one additional agent that treats, prevents or reduces the symptoms of the lung fibrosis and/or acute lung injury.

In certain embodiments, the subject is a mammal. In other embodiments, the mammal is a human.

The invention further provides a method of evaluating efficacy of a drug in treating ALI.

In certain embodiments, the method comprises contacting a neutrophil with the drug and measuring neutrophil ROS production levels after the contacting. If the neutrophil ROS production levels increase after the contacting, the drug is efficacious in treating ALI.

The invention further provides a method of evaluating efficacy of a drug in treating a subject suffering from ALI. In certain embodiments, the method comprises measuring neutrophil ROS production levels in the subject after being administered the drug. If the neutrophil ROS production levels in the subject after being administered the drug are higher than the neutrophil ROS production levels in the subject before being administered the drug, the drug is efficacious in treating ALI in the subject.

Kits

The invention includes a kit comprising pazopanib, or a salt or solvate thereof, an applicator, and an instructional material for use thereof. The instructional material included in the kit comprises instructions for preventing or treating lung fibrosis and/or acute lung injury, or any other disease or disorder contemplated within the invention. The instructional material recites the amount of, and frequency with which, the pazopanib, or a salt or solvate thereof, should be administered to the subject. In other embodiments, the kit further comprises at least one additional agent that treats, prevents or reduces the symptoms of lung fibrosis and/or acute lung injury.

Combination Therapies

In certain embodiments, the compounds of the invention are useful in the methods of the invention in combination with at least one additional compound and/or therapy useful for treating or preventing lung fibrosis and/or acute lung injury. This additional compound may comprise compounds identified herein or compounds, e.g., commercially available compounds, known to treat, prevent or reduce the symptoms of lung fibrosis and/or acute lung injury.

Non-limiting examples of additional therapies contemplated within the invention include low tidal volume ventilation, which is a standard care therapy for ALI/ARDS.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions of the invention include nasal, inhalational, intratracheal, intrapulmonary, and intrabronchial.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

In certain embodiments, the composition of the invention comprises a stable dry powder blend containing levothyroxine sodium hydrate; lactose particles, comprising lactose $H_2O$, gelatin and starch maize; sodium starch glycolate; magnesium stearate; and talc silicified, comprising talc purified and colloidal silicon dioxide. In other embodiments, the dry powder comprises levothyroxine sodium is in an amount 4 to 0.02 mg per 100 mg of the dry powder. In yet other embodiments, the dry powder comprises lactose in an amount higher than 90 mg per 100 mg of the dry powder preparation. In yet other embodiments, the dry powder comprises lactose particles consisting of lactose $H_2O$, gelatin and starch maize, wherein the ratio by weight-mg of: "lactose $H_2O$":"gelatin":"starch maize" is 55-75:0.20-0.80:20-40. In yet other embodiments, the dry powder comprises sodium starch glycolate in an amount of 4-8 mg per 100 mg of dry powder. In yet other embodiments, the dry powder comprises magnesium stearate in an amount of 0.5-2 mg per 100 mg of dry powder. In yet other embodiments, the dry powder comprises talc silicified, in an amount of 2 mg per 100 mg of dry powder, wherein the talc silicified comprises talc purified and colloidal silicon dioxide in an amount of 0.667 mg of talc purified and 1.333 mg of colloidal silicon dioxide for 2 mg of talc silicified. In yet other embodiments, the blend further comprises a lake. In yet other embodiments, the dry powder comprises sodium starch glycolate in an amount of 5-6 mg per 100 mg of dry powder. In yet other embodiments, the dry powder comprises magnesium stearate in an amount of 1 mg per 100 mg of dry powder.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and/or treatment conditions with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods:
Materials

The following reagents were purchased from Sigma: N-Formyl-L-methionyl-L-leucyl-L-phenylalanine (fMLP), Phorbol 12-myristate 13-acetate (PMA), Lipopolysaccharide (LPS), Butylated Hydroxyanisole (BHA), Lysolecithin, Paraformaldehyde (PFA), FITC Albumin, Horse Reddish Peroxidase (HRP), and Isoluminol. Percoll was purchased from GE Healthcare (Uppsala, Sweden), Bovine Serum Albumin (BSA) was purchased from American Bio (Natick, Mass.), GMCSF was purchased from Peprotech, Lipofectamine kit and Cell trace dyes were purchased from Thermo Fisher. The following material was purchased from GIBCO: Dulbecco's Modified Eagle Medium (DMEM), Hanks Balanced Salt Solution (HMS), Phosphate Buffered Saline (PBS).

The commercial antibodies used in the study are: GST antibody (2624, Cell signaling), His antibody (2366, Cell Signaling), HA antibody (MMS-101R, Covance), Myc antibody (MMS-150R, Covance), anti-phospho-AKT antibody (4060 and 2965, Cell Signaling), anti-AKT antibody (9272, Cell Signaling), anti-MEKK3 antibody (5727, Cell Signaling), anti-p47$^{phox}$ antibody (17875, Santa Cruz), anti-CD31 antibody (102502, BioLegend), anti-α-smooth muscle actin antibody (ab8211, Abcam), and anti-β-actin antibody (4967, Cell Signaling). The rabbit polyclonal anti-S208 p47$^{phox}$ was acquired from Abiocode. Protein A/g PLUS-agarose beads were purchased from Sant Cruz Biotechnology (Santa Cruz, Calif.). ELISA kits for cytokine measurements were purchased from eBioscience (San Diego, Calif.). The cDNAs for MAP3K3 and p67$^{phox}$ were acquired from ADDGENE, and cDNAs for p47$^{phox}$ and gp91$^{phox}$ from Open Biosystems.

Mice

The MEKK2$^{-/-}$ mice were previously described in Guo, et al., 2002, Mol. Cell Biol. 22:5761-5768, whereas the MEKK3" mice were described in Wang, et al., 2009, J. Immunol. 182:3597-3608. Both MEKK2$^{-/-}$ and MEKK3$^{fl/fl}$ are in C57B1 background. Myeloid cell specific MEKK3 KO mice, MEKK3$^{m/m}$, were generated by intercrossing MEKK3$^{fl/fl}$ mice with the B6.129-Lyzs$^{tm1(cre)Ifo}$/J mice from Jackson Lab. The double knockout (DKO) mice, MEKK2$^{-/-}$ MEKK3$^{m/m}$, were generated by intercrossing MEKK2$^{-/-}$ mice with MEKK3$^{m/m}$ mice. Wild type (WT) mice, C57BL6, were purchased from Taconic laboratories (Germantown, N.Y.). The BHA (W218308, Sigma-Aldrich)-containing chow (0.75% w/w BHA) was custom-made by Harlan Laboratories from 2018S diet and sterilized by irradiation.

Neutrophil Preparation and Transfection

Mice were euthanized in a $CO_2$ chamber according to approved protocol, bone marrow was harvested from long bones of the mice, red blood cells (RBCs) were lysed with ACK buffer (155 mM $NH_4Cl$, 10 mM $KHCO_3$ and 127 μM EDTA), the cells were layered on a discontinuous Percoll gradient composed of 81%, 62% and 45% Percoll layers, and the cells were isolated from the interphase between 81% and 62% Percoll layers. Cells were washed in MSS and used for various assays.

For neutrophil transfection, neutrophils ($3 \times 10^6$ cells/100 µl) and up to 1.6 µg of DNA were suspended in the supplied nucleofection solution and electroporated in Nucleofector device 2b (Lonza, Switzerland). The samples were then cultured overnight in the medium (RPMI 1640, 10% FBS (V/V), GMCSF 25 ng/ml) at 37° C. in humidified air with 5% $CO_2$.

Dunn Chamber Chemotaxis Assay

WT (stained with Cell Trace Calcein Red-Orange dye) and DKO neutrophils ($1.25 \times 10^6$ cells/ml) were suspended in an assay buffer (0.25% BSA in MSS with $Ca^{2+}$ and $Mg^{2+}$), and vice versa. An aliquot of cells was then allowed to adhere for 15 minutes on fibrinogen coated coverslips, the coverslip was inverted on the Dunn Chamber with assay buffer in the inner well and fMLP (10 µM) in the outer well, and time lapse images were recorded at 30 sec intervals for 30 minutes under Olympus BX61 microscope. The cellular tracks were analyzed as reported in Konstandin, et al., 2006, J. Immunol. Meth. 310:67-77.

Integrin Expression Assay

Bone marrow-derived neutrophils were resuspended in flow cytometry buffer (PBS with 1% BSA), stimulated with fMLP (5 µM) for indicated durations, fixed with 4% PFA and then stained with FITC labeled anti LFA-1 or anti Mac-1. Samples were analyzed by BD LSR II flow cytometer.

ICAM-1 Binding Assay

The assay was carried out as described in Wang, et al., 2008, J. Clin. Invest. 118:195-204. The ICAM-1-Fc-F(ab')2 complexes were generated by incubating Cy5-conjugated AffiniPure goat anti-human Fcγ fragment-specific IgG F(ab')2 fragments (Jackson Immunobiology) and ICAM-1-Fc (100 µg/ml, R&D) at 4° C. for 30 min in PBS. Neutrophils, which were resuspended at $0.5 \times 10^6$ cells/ml in PBS containing 0.5% BSA, 0.5 mM $Mg^{2+}$ and 0.9 mM $Ca^{2+}$, were mixed with the ICAM-1-Fc-F(ab')2 complexes in the presence or absence of fMLP for durations specified in the figure legends. The reactions were terminated by adding 4% paraformaldehyde. After 5 min, fixation was stopped by adding 3-ml ice-cold FACS buffer. Cells were pelleted, resuspended in 300 µl of FACS buffer, and analyzed on a flow cytometer.

Neutrophil Infiltration into Inflamed Peritonea and Flow Chamber Adhesion Assay

For the peritonitis infiltration model, purified wild type and mutant neutrophils were labeled with 2.5 µM CFSE [5-(and -6)-carboxyfluorescein diacetate succinimidyl esters] and 2.5 µM Far-Red DDAO SE, respectively, and vice versa. The WT and mutant cells with different fluorescence labels were mixed at a 1:1 ratio and injected into retro-orbital venous sinus of wildtype littermates, which were injected with 2 ml of 3% Thioglycolate (TG) two hours earlier. The mice were euthanized one and half hour later. Cells in their peritonea were collected and analyzed by cell counting and flow cytometry. The data presented are the combination of the experiments with reciprocal fluorescence labeling.

To examine neutrophil adherence to endothelial cells under shear stress, mouse endothelial cells (Wang, et al., 2008, J. Clin. Invest. 118:195-204) were cultured to confluency on 10 µg/ml fibronectin coated coverslips and treated with 50 ng/ml TNFα for 4 hours. The coverslips containing the endothelial cell layer were washed with PBS and placed in a flow chamber apparatus (GlycoTech). The WT and mutant cells labeled different fluorescence labels as described elsewhere herein were mixed at a 1:1 ratio and flowed into the chamber at a shear flow rate of 1 dyn/$cm^2$. The adherent cells were then examined and counted under a fluorescence microscope.

ROS Release Assay

Neutrophils were suspended in a reaction mixture (0.25% BSA in MSS with $Ca^{2+}$ and $Mg^{2+}$, 10 mM Isoluminol, 100µ/ml HRP), distributed cells in the well of a 96 well plate, and stimulated with fMLP (10 µM). Isoluminol-enhanced chemiluminescence was recorded continuously in a plate reader (Perkin Elmer). For restituted ROS production system in COS-7 cells, PMA (2 µM) was used for stimulation.

Neutrophil Degranulation Assay

One million neutrophils were incubated with 10 µM CB for 5 min at 37° C. prior to stimulation with fMLP (500 nM) for another 10 min. The reaction was stopped by being placed on ice, and the suspension was centrifuged at 500×g for 5 min at 4° C. Supernatants were assayed for MPO and MMP contents using the EnzChek Myeloperoxidase Activity Assay Kit and EnzChek Gelatinase/Collagenase Assay kit (Life Technologies, Grand Island, N.Y.), respectively (Li, et al., 2009, Blood 113:4930-4941; Lee, et al., 2007, Am. J. Physiol. Lung Cell. Mol. Physiol. 292:L799-812).

LPS-Induced Lung Injury

Mice were anesthetized with ketamine/Xylazine (1 gm/kg and 100 mg/kg) and were allowed to inhaled 50 µl of LPS (1 mg/ml) placed as droplets on nares. Mice postures were maintained upright. Twenty-two hours after the induction of injury, 100 µl of FITC-labeled albumin (10 mg/ml) were injected via retro-orbital vein, and 24 hours after the induction of injury, mice were euthanized by exsanguination. To obtain bronchoalveolar lavage fluid, 1 ml of PBS was instilled into lungs and retrieved a via a tracheal catheter. In some experiments, mice were first fed with antioxidant BHA in food (Harlan Laboratory Services) for 7 days before the induction of lung injury.

Acid Aspiration-Induced Lung Injury

Mice were anaesthetized by ketamine/Xylazine (1 gm/kg and 100 mg/kg) and were suspended vertically from their incisors on a custom-made mount for orotracheal instillation. A 22G catheter (Jelco, Smiths Medical) was guided 1.5 cm below the vocal cords, and 2.5 µl/g of 0.05 M HCl was instilled. Two hours after the induction of injury, 100 µl of FITC-labeled albumin (10 mg/ml) was injected via retro-orbital vein. Measurements were made 6 hours after the induction of injury. Control animals received saline instead of HCl in the same manner. In survival experiments, mice received 2.5 µl/g of 0.1 M HCl orotracheally and the observation period was extended up to 30 h. To examine pharmacological intervention, MEKK2/3 inhibitor pazopanib were used 1 h after HCl instillation.

GST Pulldown Assay

Recombinant proteins were expressed in E. coli and purified by affinity chromatography. The proteins were then incubated in 200 µl of the binding buffer (10 mM HEPES pH 7.4, 150 mM NaCl, 1% Triton, 0.12% SDS, 1 mM dithiothreitol, 10% glycerol, lx protease inhibitor cocktail) at 4° C. overnight on a shaker. Next morning, glutathione beads were added to the protein mixture for additional 2 h. After extensive washes, proteins on the beads were resolved by SDS/PAGE and detected by Western Blot.

MAP3K3 Kinase Assay

In 50 µl reaction buffer (100 mM Tris-HCl pH 7.4, 50 mM EGTA, 100 mM $MgCl_2$), 100 ng of recombinant MAP3K3 were incubated with immune-precipitated substrate proteins, [γ-$^{33}$P]-ATP (10 µCi), and cold ATP (50 µM) at 37° C. for 30 minutes. The reaction was stopped by adding the SDS loading buffer. The samples were boiled for 5 minutes. The proteins were separated by SDS-PAGE, and were visualized and quantified by a phosphoimager.

Adoptive Bone Marrow Transfer

Marrows were harvested from the long bones of WT and DKO donor mice, RBCs were lysed with ACK buffer (155 mM NH$_4$Cl, 10 mM KHCO$_3$ and 127 µM EDTA), cells were suspended in sterile normal saline and intravenously injected into irradiated (9.5 Grays, γ radiation) recipient WT mice (5×10$^6$ cells/mouse). The mice were provided with autoclaved food and water containing Sulfatrim (48 mg/ml) for four weeks. These mice (HS-DKO and WT control) were used for experimental purposes 8 weeks after transplantation.

Human Neutrophils

Buffy coat of human blood samples were subjected to neutrophil enrichment using the EasySep Human Neutrophil Enrichment Kit (Stemcell Technologies) according to manufacturer's protocol. Briefly, the depletion antibody cocktail was mixed with the buffy coat followed by incubation with magnetic particles. The EasySep Magnet was then used to immobilize unwanted cells as the label-free neutrophils were poured into another conical tube. Enriched neutrophils were pelleted and resuspended in an assay buffer (Hanks buffer with Ca$^{2+}$ and Mg$^{2+}$, 0.25% BSA) for ROS production assay.

Bi-Layer Co-Culture of Neutrophils with Endothelial Cells

Mouse endothelial cell (MEFC; Paik, et al., 2004, Genes Dev. 18:2392-2403) were first plated on the outside of the polycarbonate membrane (25,000 cells/cm$^2$) of the Transwell inserts (24-well type, 0.4-µm pore size, Corning, Inc. 353095), and placed upside down in the wells of the culture plate. After the endothelial cells had adhered, the Transwell inserts were inverted and reinserted into the wells of the plate. The medium was replaced 24 h after seeding with serum-free medium. SOD (60 U/ml), catalase (100 U/ml) or mock were added to the lower chambers 2 h later for 30 min. Mouse neutrophils stimulated with 5 µM fMLP were then plated on the top surface of the insert (6×10$^6$ cells/cm$^2$) for 30 min. At the end of the incubation period, neutrophils on the top side of the inserts were scraped, and endothelial cells on the other side of the inserts were lysed with SDS-PAGE sample buffer for Western analysis.

Trans-Endothelial Electrical Resistance (TEER) Measurement

ECIS 8W10E+ arrays (Applied BioPhysics) were coated with 10 µg/ml of poly-D-lysine (PDL) and washed with sterile water. Complete EBM-2 media (300 µl) was added to each well for a quick impedance background check. Subsequently, immortalized mouse pulmonary endothelial cells (Murata, et al., 2007, J. Biol. Chem. 282:16631-16643) were seeded in a density of 60,000 cells/well in 300 µl EBM-2 medium in the coated arrays and incubated them at 37° C. in a CO$_2$ incubator. Electrical resistance of the cell layer was recorded continuously on an ECIS system (Applied BioPhysics) until a stable resistance of approximately 600-700 ohms was achieved, after which media were removed from wells and replaced with 100 µl of assay buffer (Hanks buffer with Ca$^{2+}$ and Mg$^{2+}$, 0.25% BSA). Cells were allowed to re-equilibrate at 37° C. for 2 hours, before 1 µl of SOD (60 U/ml), catalase (100 U/ml) or mock were added to wells for 30 min followed by addition of 50 µl of mouse neutrophils in assay buffer containing 5 µM fMLP. Data were collected real-time throughout the experiment. All ECIS measurements were analyzed at an AC frequency of 4 kHz, which was identified as the most sensitive frequency for this cell type by frequency scans along an entire frequency range (1 kHz-64 kHz). The TEER values were normalized against those co-cultured with WT neutrophils treated with mock.

Statistical Methods

Data were analyzed with Prism software. For two samples, t test was used; for multiple samples, ANOVA was used with p values set at <0.05 as being significant.

Example 1: MAP3K2/3-Deficiency Ameliorates LPS-Induced Lung Injury

Gene expression analysis indicates that the MAP3K3 gene is specifically expressed in human myeloid cells (www dot biogps dot org). In addition, its expression is down-regulated in neutrophils from the lung exudates of human subjects inhaled with endotoxin. Because of the importance of neutrophils in acute lung injury, the role of MAP3K3 in myeloid cell functions and acute lung injury was investigated using a mouse acute lung injury (ALI) model.

Figure 1A:
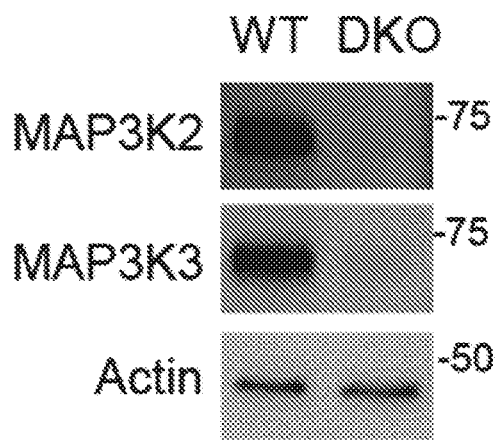
FIGS. 1A-1H illustrate loss of MAP3K2 in hematopoietic cells and MAP3K3 in myeloid cells ameliorates LPS-induced lung injury.

In mice, the Map3k3 gene is expressed abundantly in various hematopoietic cells with its expression being highest in myeloid cells (www dot immgen dot org). Myeloid-specific knockout (KO) of Map3k3 was generated by crossing Map3k3$^{fl/fl}$ and lysozyme-Cre mice. However, significant neutrophil or lung injury phenotypes were not observed with Map3k3-deficiency. Without wishing to be limited by any theory, MAP3K3 function may be compensated by its close homolog MAP3K2, which is also expressed in mouse myeloid cells (www dot immgen dot org) and, like MAP3K3, could be readily detected in neutrophils by Western analysis (FIG. 1A).

Thus, both kinases were inactivated, and subsequently a global MAP3K2 knockout (KO) and myeloid-specific MAP3K3 KO mouse line (DKO) was generated by crossing the Map3k2$^{-/-}$ mice with myeloid-specific Map3k3$^{-/-}$ mice. To limit contributions of MAP3K2 from non-hematopoietic cells, adoptive transfer of the DKO bone marrow (BM) to lethally irradiated wildtype (WT) recipient mice was performed. The resultant mice are designated as HS-DKO. Western analysis shows the lack of the MAP3K2 and MAP3K3 proteins in the neutrophils isolated from the HS-DKO mice (FIG. 1A).

Figure 1B:
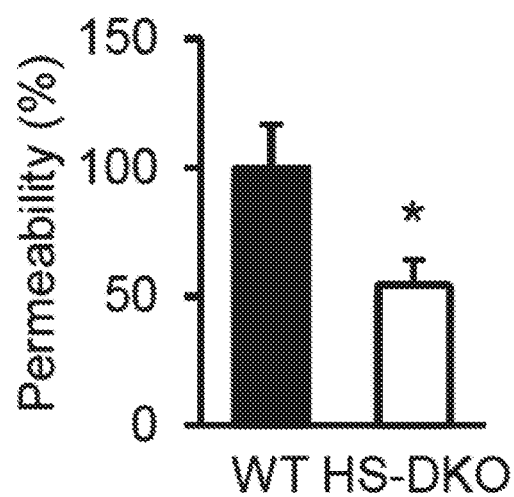
Figure 1C:
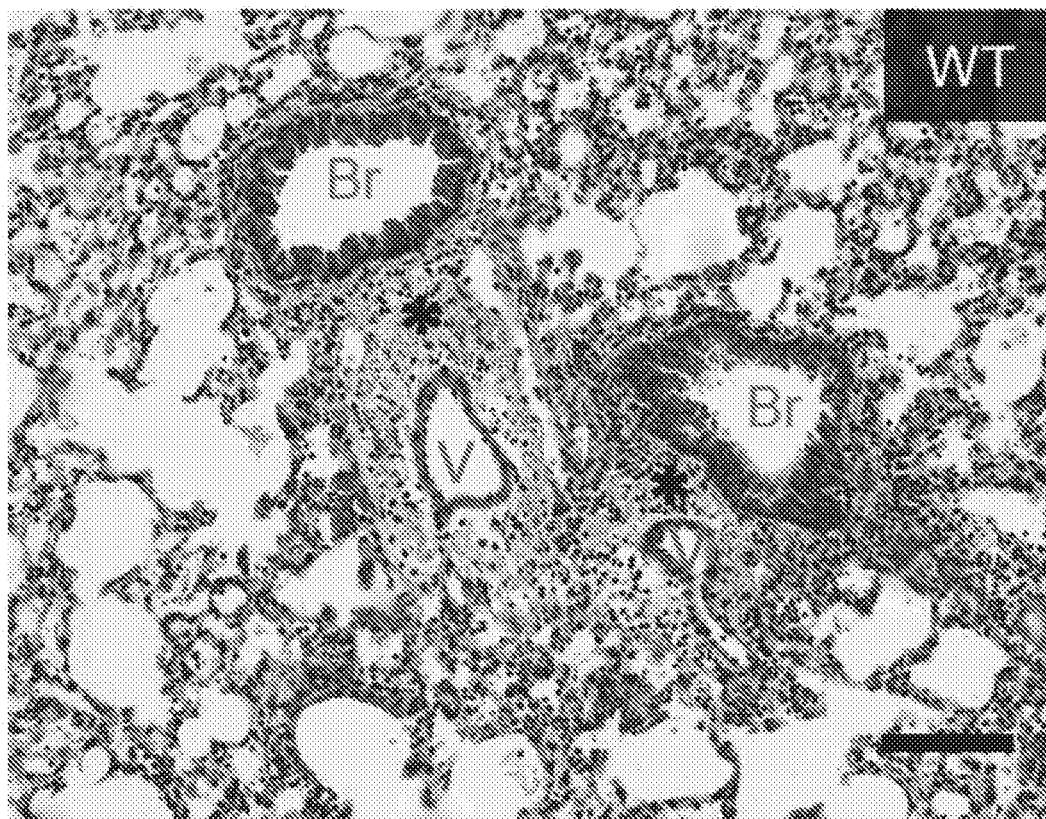
Figure 1D:
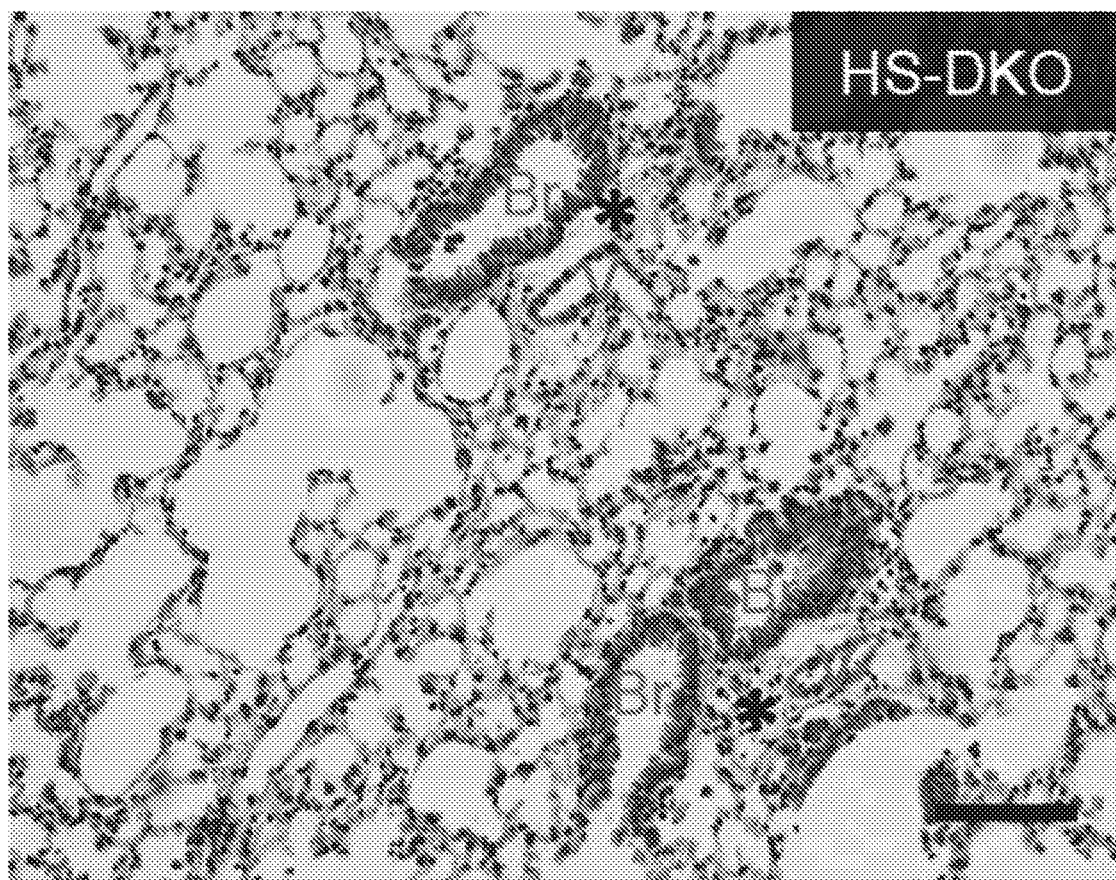
Figure 1E:
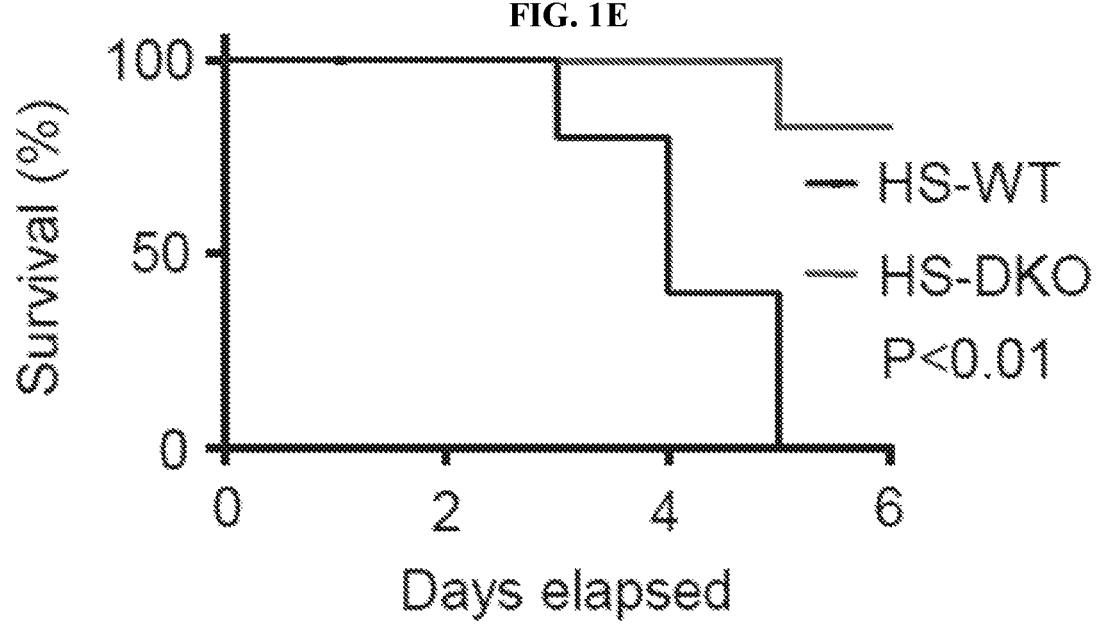
Figure 1F:
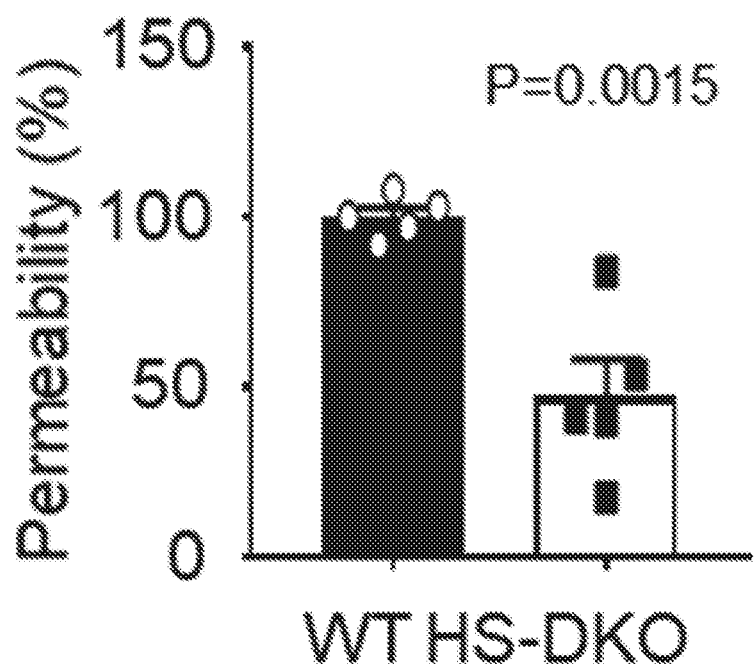
Figure 1G:
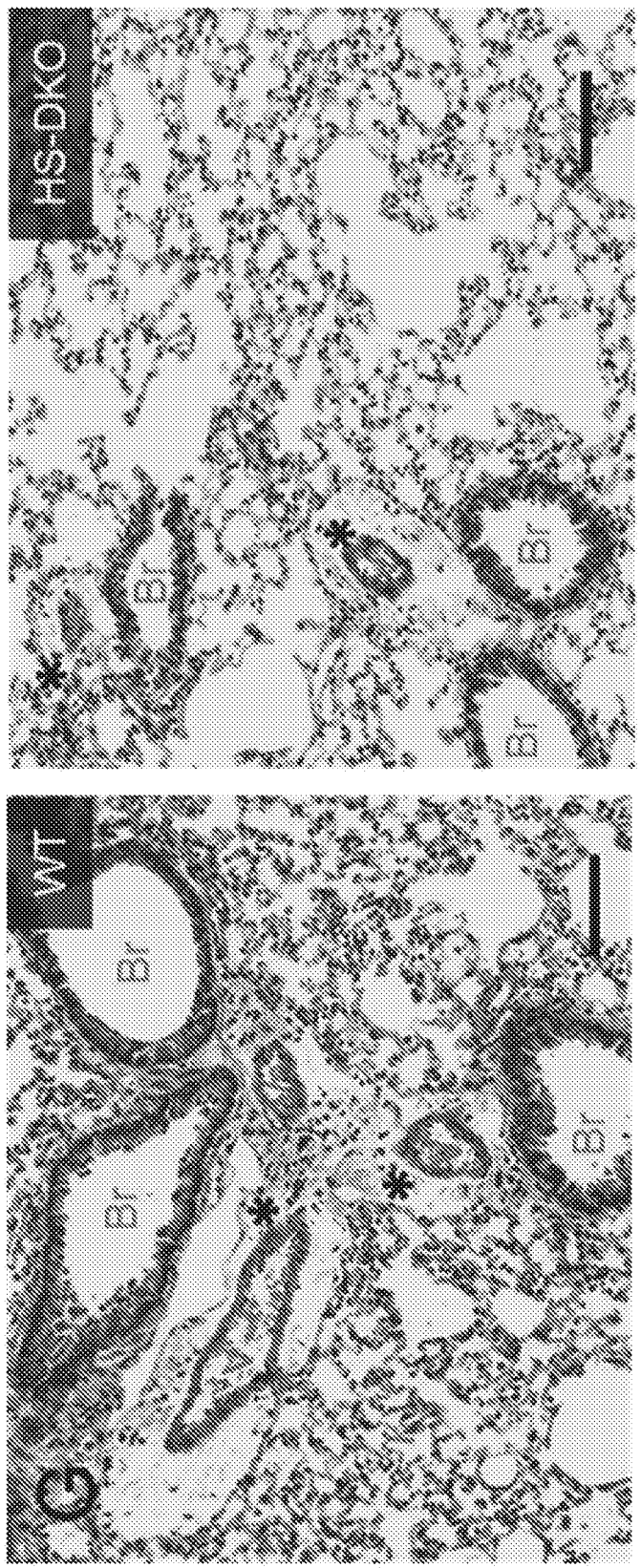
Figure 1H:
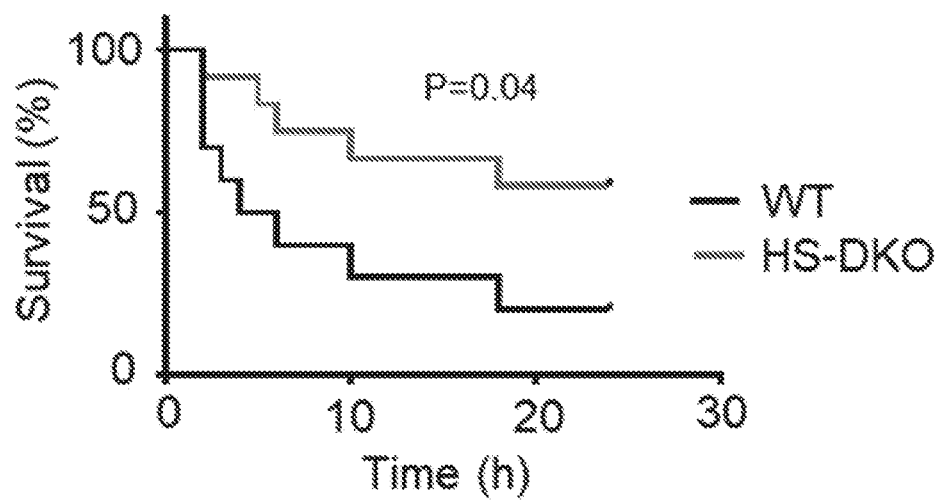
Figure 8A:
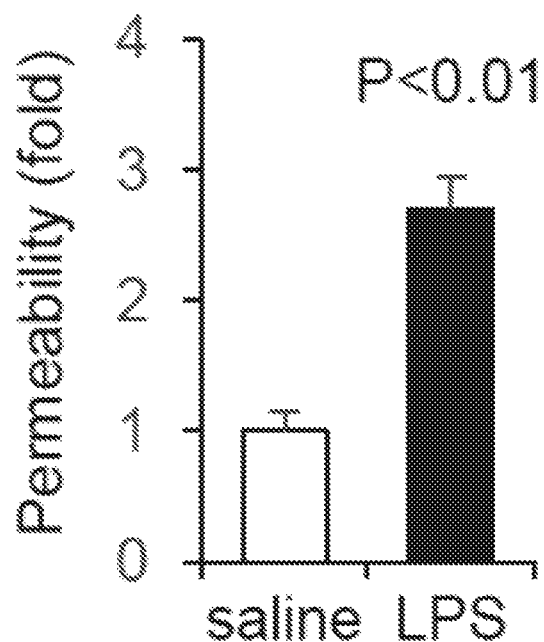
FIGS. 8A-8E illustrate the finding that loss of MAP3K2 in hematopoietic cells and MAP3K3 in myeloid cells does not affect the number of infiltrated myeloid cells or contents of cytokines in BALF of LPS-injured lungs.
Figure 8B:
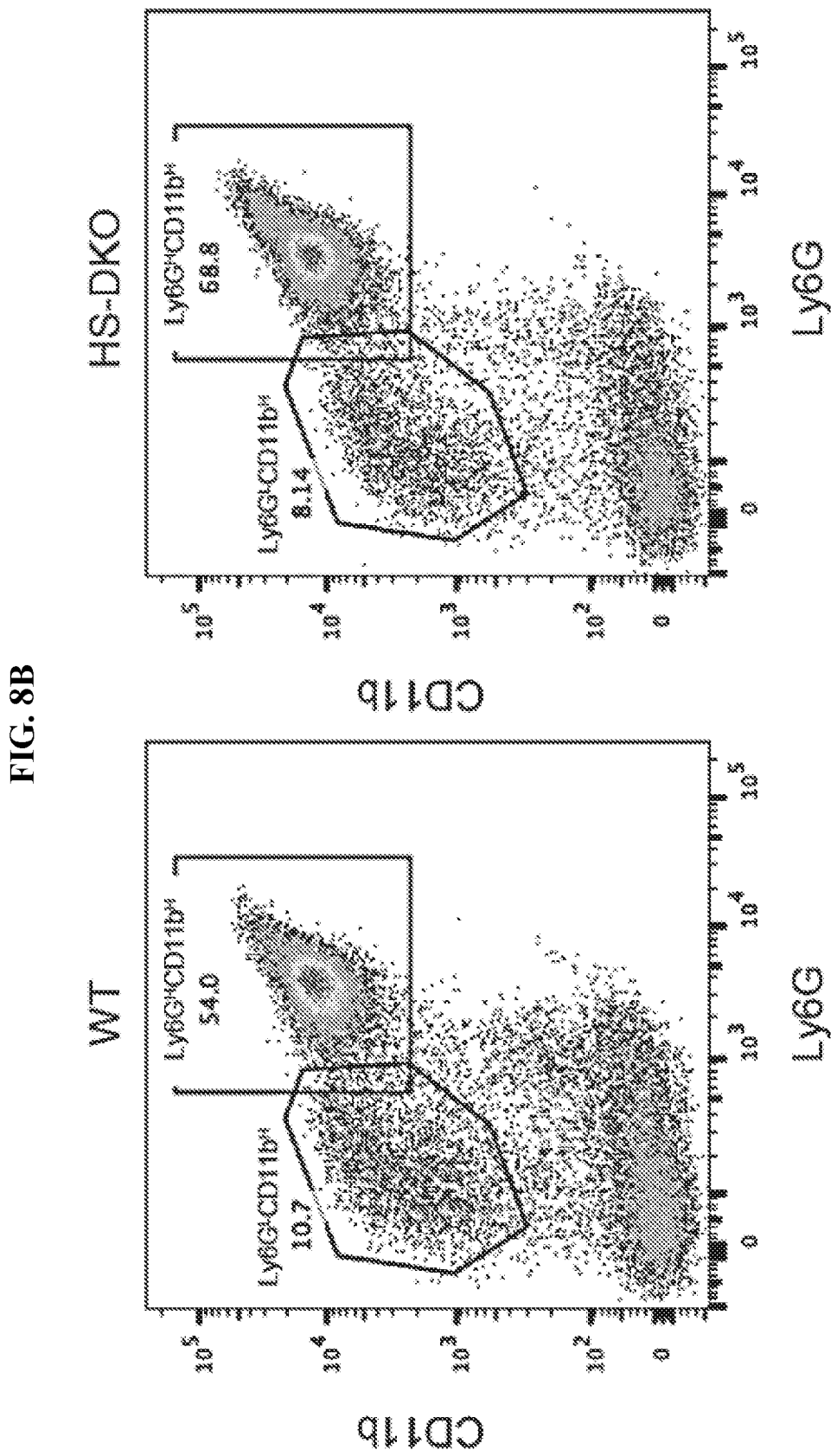
Figure 8C:
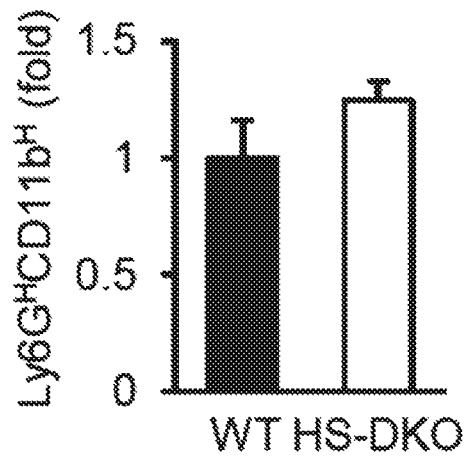
Figure 8D:
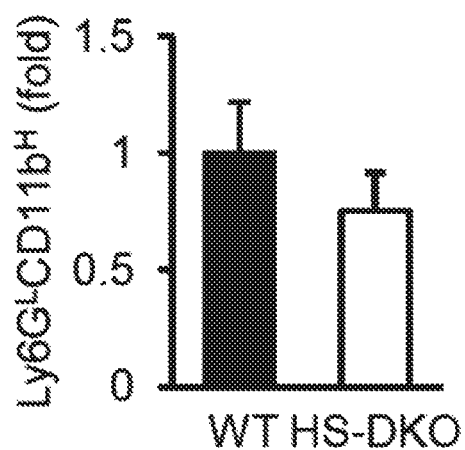
Figure 8E:
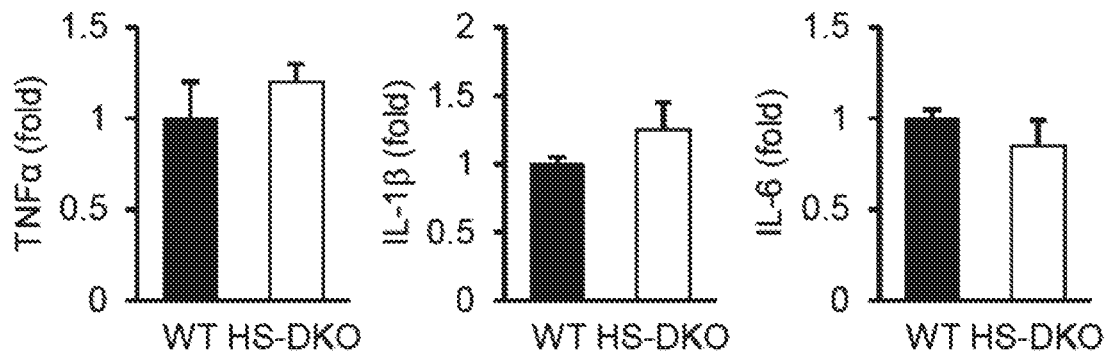
Figure 8F:
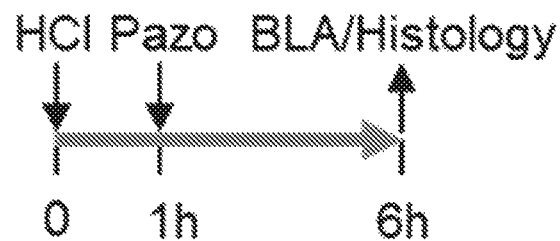
FIGS. 8F-8J illustrate the finding that loss of MAP3K2 in hematopoietic cells and MAP3K3 in myeloid cells does not affect the number of infiltrated myeloid cells or contents of cytokines in BALF of HCl-injured lungs.
Figure 8G:
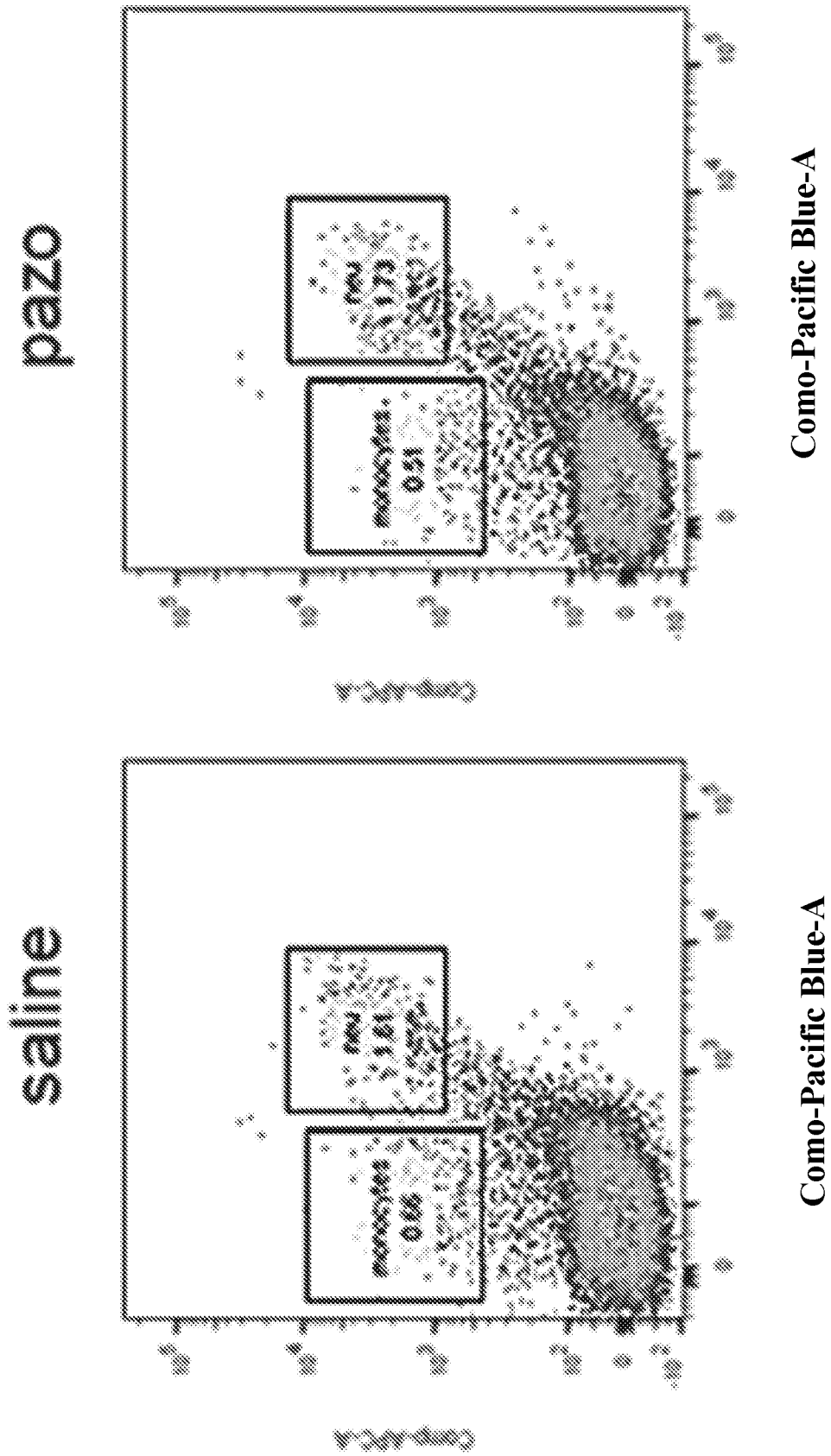
Figure 8H:
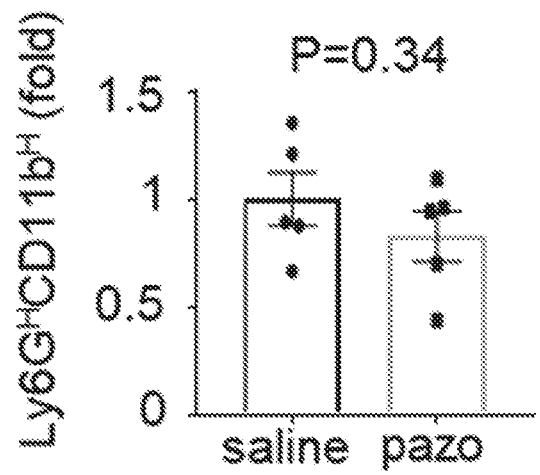
Figure 8I:
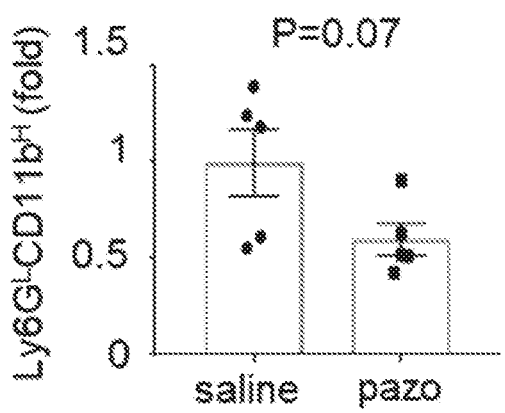
Figure 8J:
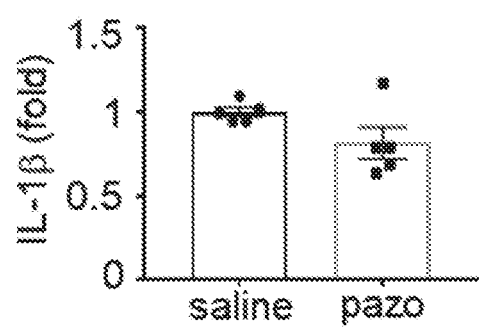

The HS-DKO mice were subjected to LPS-induced lung injury. This murine model recapitulates the hallmarks of human ALI including neutrophilic influx into the alveolar space, pulmonary edema, increased lung permeability (FIG. 8A), and high mortality. When the HS-DKO mice and control WT mice, which received WT BM transfer, were treated with LPS via nasal instillation, the HS-DKO mice sustained significantly reduced lung injury compared to the wildtype (WT) control mice, evidenced by reduced permeability, edema and alveolar wall thickening (FIGS. 1B-1D). The HS-DKO mice also showed reduced mortality compared to the WT control mice (FIG. 1E). The same results were also observed when HCl-ALI model was used; the lack of MEKK2/3 reduced lung permeability and damage and extended survival (FIGS. 1F-1H). There was no significant difference in the numbers of myeloid cells in the bronchoalveolar lavage fluid (BALF) between the HS-DKO and WT control mice (FIGS. 8B-8D). In addition, there were no significant differences in the contents of TNFα, IL-1β or IL-6 in BALFs (FIG. 8E). No differences in myeloid infiltration or IL-1b level in BALF were observed when the HCl model was used (FIG. 8F-J). Together, these results suggest that the lack of MAP3K3 in myeloid cells and MAP3K2 in hematopoietic cells largely affects pulmonary permeability rather than myeloid infiltration or cytokine production in injured lungs.

Example 2: MAP3K2/3-Deficiency Specifically Alters Neutrophil ROS Release

Figure 2A:
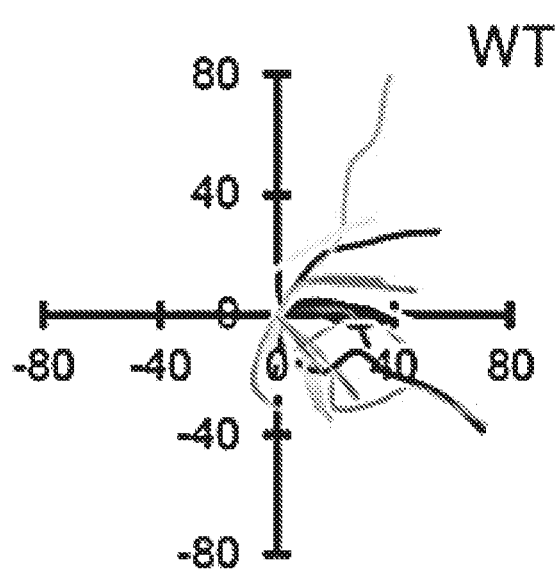
FIGS. 2A-2K illustrate the finding that MAP3K2/3-null neutrophil show normal chemotaxis, endothelial cell adhesion, integrin expression and activation, infiltration and degranulation.
Figure 2B:
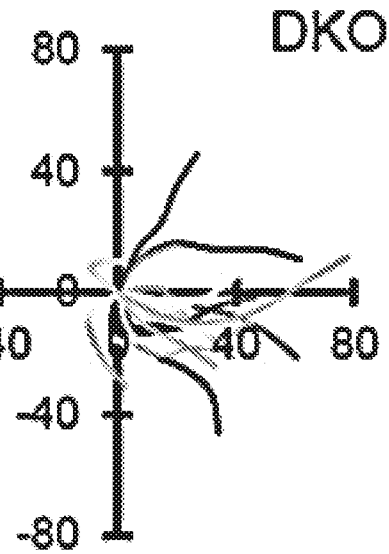
Figure 2C:
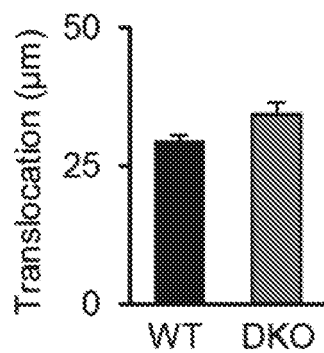
Figure 2D:
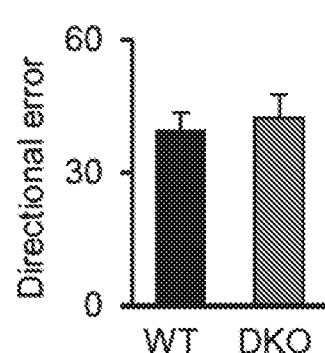
Figure 2E:
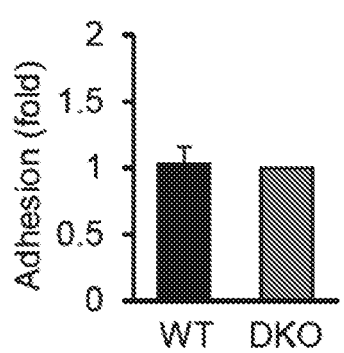
Figure 2F:
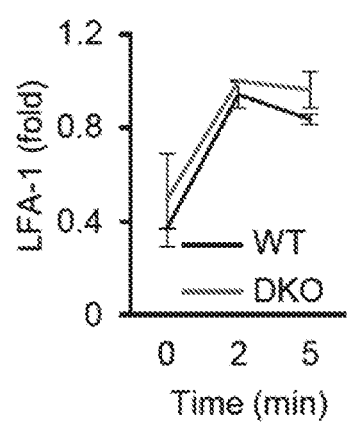
Figure 2G:
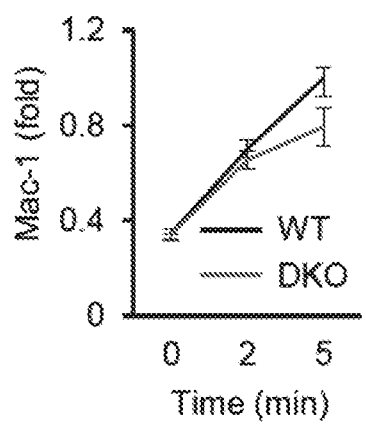
Figure 2H:
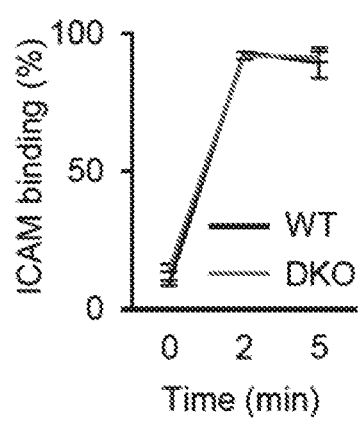
Figure 2I:
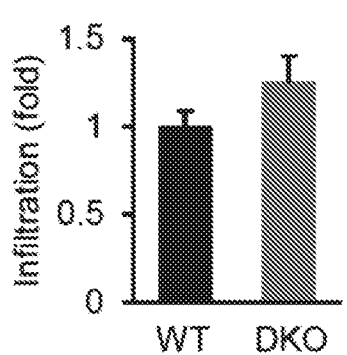
Figure 2J:
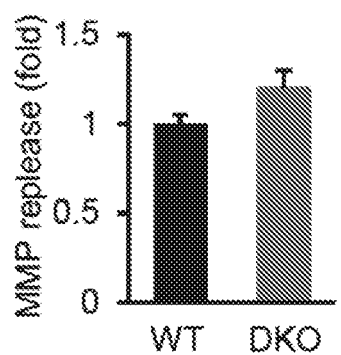
Figure 2K:
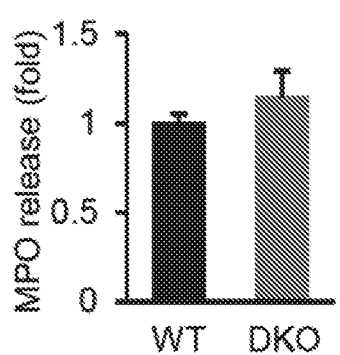
Figure 3A:
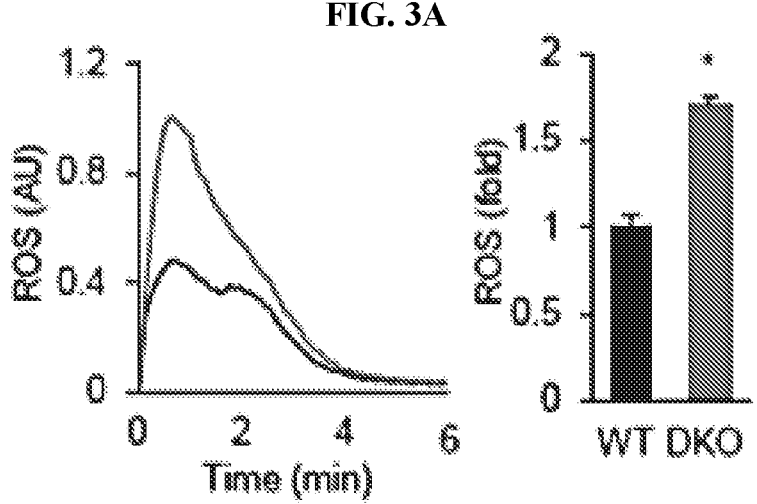
Figure 3B:
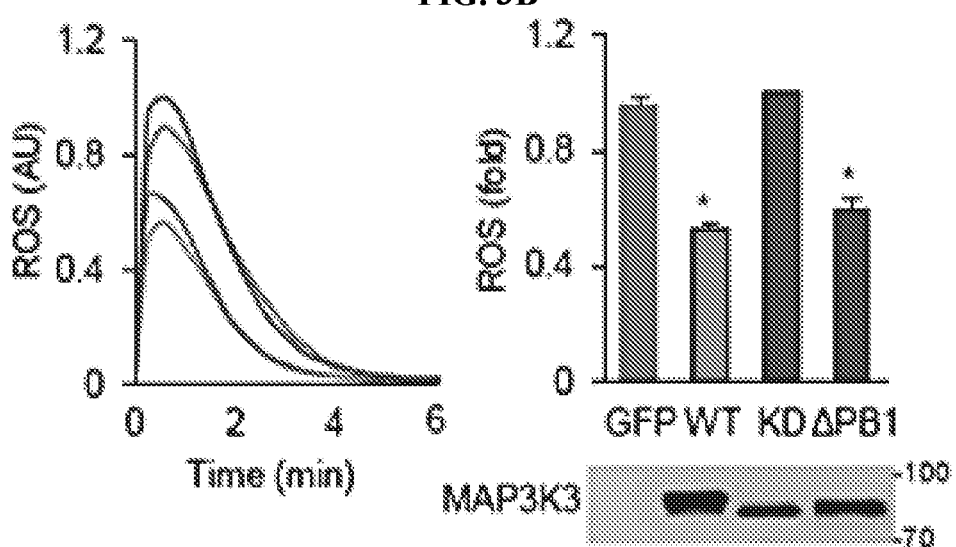
Figure 3C:
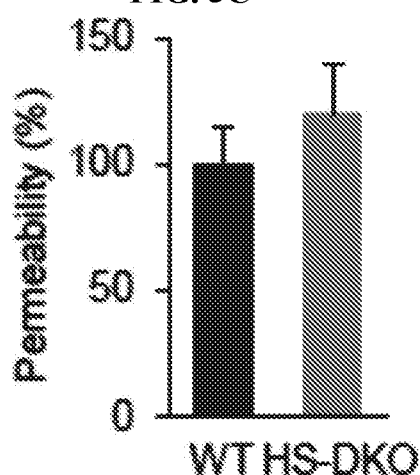

Consistent with the lack of an effect on neutrophil infiltration into BALF by MAP3K2/3-deficiency, the deficiency did not affect neutrophil chemotaxis in in vitro (FIGS. 2A-2D). Neither did it affect neutrophil adhesion to endothelial cells (FIG. 2E), nor expression or activation of β2 integrins (FIGS. 2F-2H). There was also no difference between WT or MAP3K2/3-deficient neutrophils in infiltration into inflamed peritonea, a model for testing neutrophil infiltration in vivo (FIG. 2I). In addition, MAP3K2/3-deficiency did not alter neutrophil degranulation (FIGS. 2J-2K). However, the MAP3K2/3-deficiency led to increased production of ROS from neutrophils upon stimulation (FIG. 3A). Expression of WT, but not kinase-dead, MAP3K3 in the MAP3K2/3-deficient neutrophils could suppress the ROS release, confirming the involvement of MAP3K3 in regulation of ROS release (FIG. 3B). This result also indicates that MAP3K3 regulated-ROS release is dependent on its kinase activity. When the mice were fed with butylated hydroxyanisole (BHA), a ROS scavenger and subjected to LPS-induced injury, the difference between HS-DKO and WT control mice in permeability and edema dissipated (FIGS. 3C-3E), suggesting that the protective role of MAP3K2/3-deficiency depends on ROS.

Figure 9A:
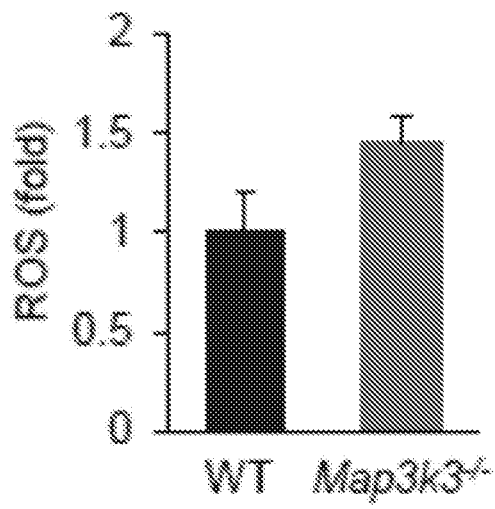
FIGS. 9A-9B illustrate ROS release from neutrophils lacking MAP3K2 or MAP3K3 upon stimulation of fMLP.
Figure 9B:
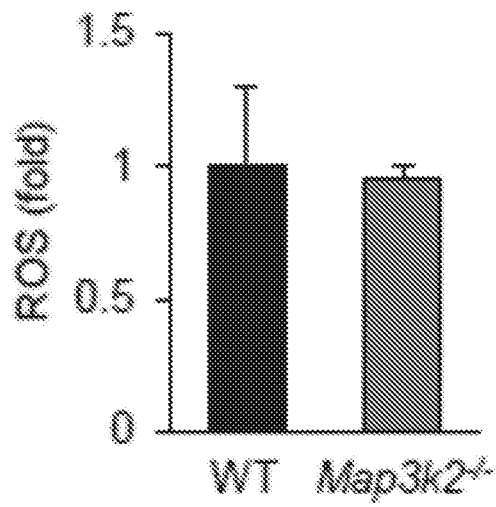

Effects of individual MAP3K2 and MAP3K3 KO on ROS release from neutrophils were also examined. MAP3K3 KO showed a trend of increases in ROS release, whereas MAP3K2 KO had no significant effect (FIGS. 9A-9B). These results confirm that these two kinases are indeed functionally redundant.

Example 3: MAP3K3 Phosphorylates $p47^{phox}$ to Inhibit ROS Production

Figure 4A:
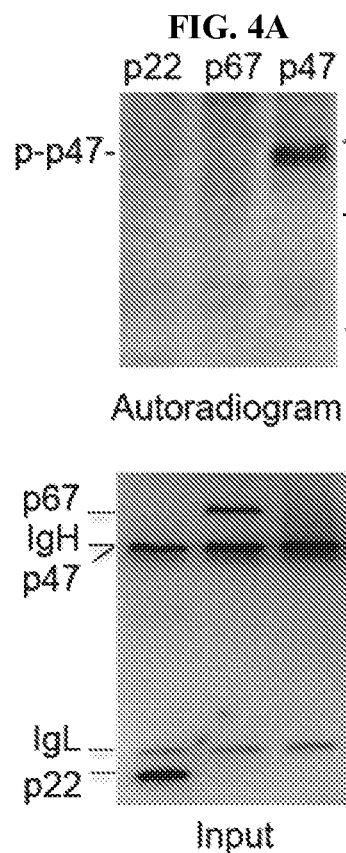
FIGS. 4A-4G illustrate the finding that MAP3K3 phosphorylates S208 of p47phox to inhibit NADPH oxidase activity.
Figure 4B:
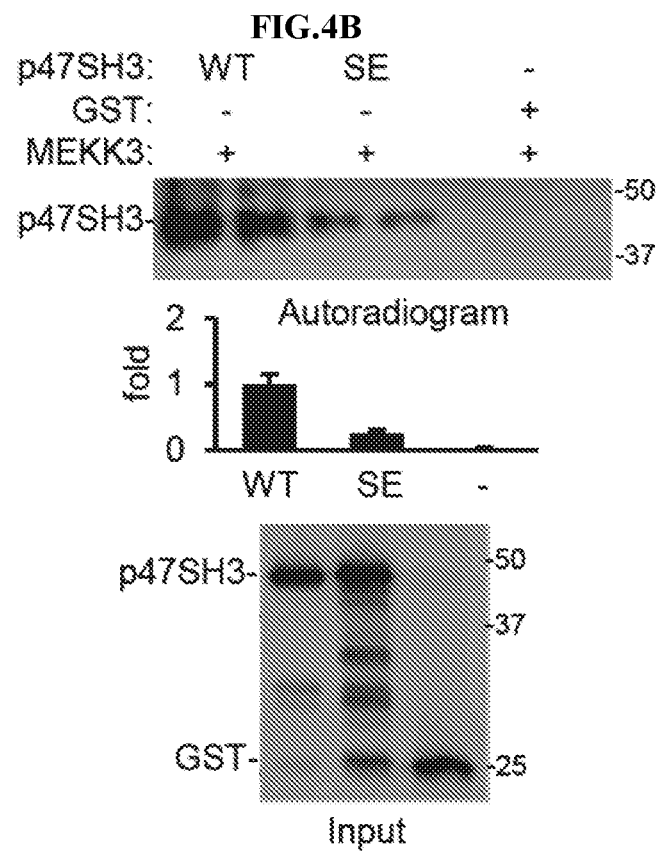

Given that the phagocytic NADPH oxidase is the major source of ROS production in neutrophils, it was tested if MAP3K3 acted through this enzyme complex. It was first investigated if the NADPH oxidase can be a substrate of MAP3K3. Recombinant proteins of MAP3K3 and several subunits of the NADPH oxidase were produced and in vitro kinase assays were carried out. Only $p47^{phox}$, but not $p22^{phox}$ or $p67^{phox}$, could be phosphorylated by MAP3K3 (FIG. 4A). Though the phosphorylation site consensus sequence for MAP3K3 is unknown, the $p47^{phox}$ sequence was analyzed using the program Scansite run with reported peptide array data for the related kinase MAP3K5 to identify likely sites of phosphorylation. This analysis predicted Ser-208 as the best scoring site among those previously observed (Obenauer, et al., 2003, Nucleic Acids Res. 31:3635-3641). When this site was mutated, MAP3K3-mediated phosphorylation was significantly reduced (FIG. 4B), indicating that this residue can indeed be phosphorylated by MAP3K3.

Figure 4C:
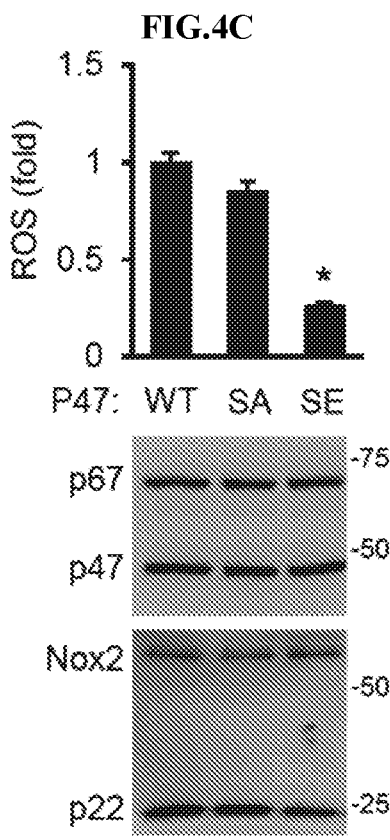
Figure 4D:
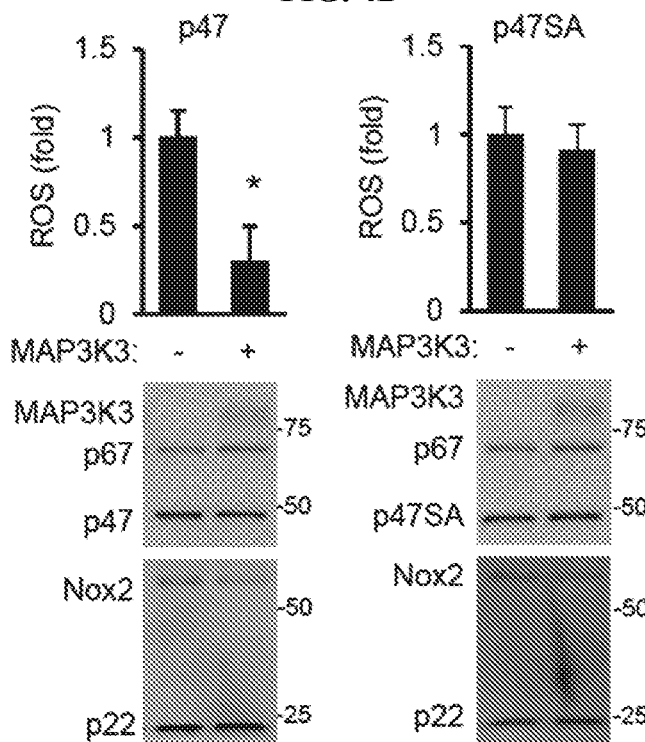

Next effects of this phosphorylation on the activity of the NDAPH oxidase were evaluated. The NADPH oxidase activity in COS-7 cells was reconstituted by expressing the NADPH oxidase subunits $p47^{phox}$, $p67^{phox}$, $p40^{phox}$, NOX2, and $p22^{phox}$ (Price, et al., 2002, Blood 99:2653-2661). These proteins are either not or insufficiently expressed in COS-7 cells. Upon addition of PMA, production of ROS could be detected from the reconstituted COS-7 cells, and this ROS production is completely dependent on the exogenous expression of $p47^{phox}$ (FIGS. 10A-10B). Expression of WT MAP3K3, but not its kinase dead mutant, inhibited ROS production in this system (FIG. 10C). Thus, a ROS production system that can be inhibited by MAP3K3 was reconstituted, similar to what happens in neutrophils. When the phospho-mimetic $p47^{phox}$ S208E mutant was used instead of WT in this reconstituted system, there was very low ROS production in comparison to WT $p47^{phox}$ (FIG. 4C). The non-phosphorylatable S208A $p47^{phox}$ mutant, by contrast, showed similar activity in the ROS reconstitution assay to the WT $p47^{phox}$ (FIG. 4C). Moreover, expression of MAP3K3 inhibited ROS production in cells expressing the WT $p47^{phox}$, but not those expressing the non-phosphorylatable S208A $p47^{phox}$ (FIG. 4D). These results together indicate that MAP3K3-mediated phosphorylation of $p47^{phox}$ at S208 inhibits the NADPH oxidase activity.

Figure 4E:
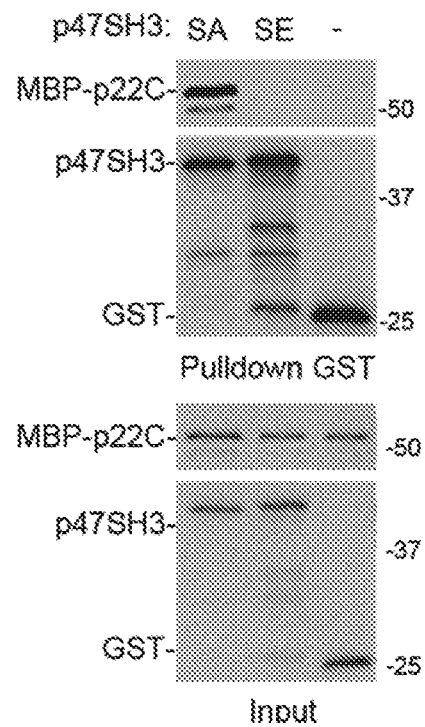

Because Ser-208 is located between two SH3 domains of $p47^{phox}$, which were involved in the interaction with $p22^{phox}$ during activation of the NADPH oxidase complex (FIG. 10D), in certain non-limiting embodiments the phosphorylation at Ser-208 can interfere with this interaction, a critical step in NADPH oxidase activation. Indeed, the phosphomimetic Ser-208 to Glu mutation abolished the interaction of $p47^{phox}$ with $p22^{phox}$ in a co-immunoprecipitation assay (FIG. 4E).

Example 4: Ser-208 of $p47^{phox}$ is Phosphorylated in Neutrophils

Figure 4F:
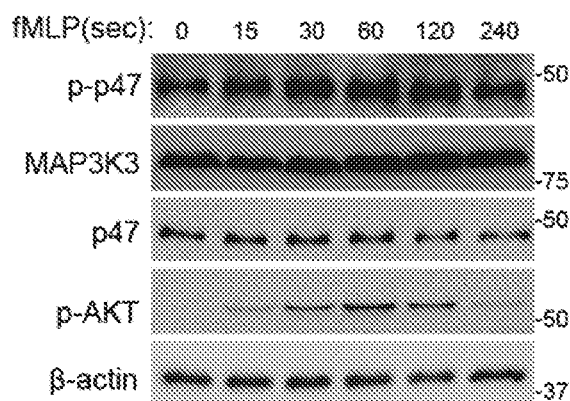
Figure 4G:
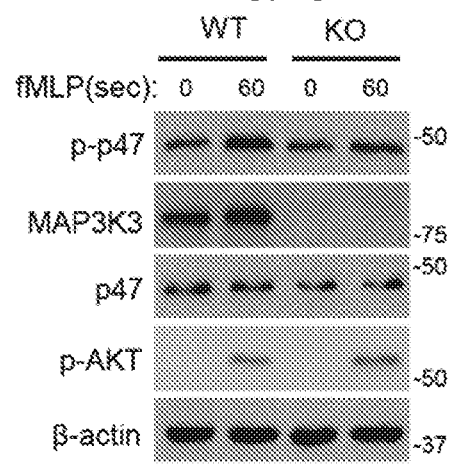

To detect if $p47^{phox}$ is phosphorylated in neutrophils by MAP3K2/3, an antibody specific for phosphorylated Ser-208 of $p47^{phox}$ was generated. Validation assay indicates that the antibody is largely specific for Ser-208-phosphorylated $p47^{phox}$, because Ser-208 mutation to alanine markedly diminishes the detection by the antibody (FIGS. 11A-11G). Using the antibody, we detected time-dependent increases in $p47^{phox}$ phosphorylation at Ser-208 (FIG. 4F). The time course of fMLP-stimulated increases in p47phox phosphorylation coincides with that of AKT phosphorylation at Ser-473 (FIG. 4F). In addition, increases in abundance of the MAP3K3 protein were observed, which may reflect its activation. The fMLP-induced increase in p47phox phosphorylation detected by this antibody was not observed in neutrophils lacking MAP3K2/3 (FIG. 4G), suggesting that fMLP induces the phosphorylation of p47phox at Ser-208 via MAP3K2/3. Without wishing to be limited by any theory, the bands detected in the DKO neutrophils by the antibody may reflect the detection of either non-phosphorylated p47phox by the antibody or basal phosphorylation of Ser-208 by other protein kinases.

Figure 4H:
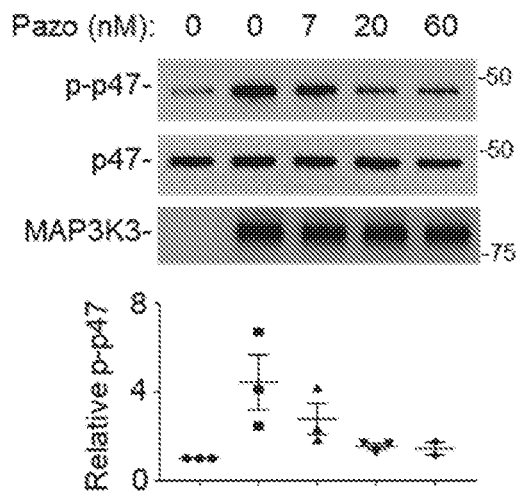
FIGS. 4H-4K illustrate the finding that pazopanib inhibits phosphorylation of p47phox by MEKK2 or 3 in an in vitro kinase assay. Recombinant p47phox prepared from an *E. coli* expression system were incubated with recombinant MAP3K2 or 3 in the presence of ATP for 30 min at 37° C. The proteins were analysis by Western blotting. The $IC_{50}$ for inhibition of phosphorylation of p47 by MAP3K2 is around 20 nM, whereas the $IC_{50}$ for MAP3K3 is around 10 nM. These numbers are far lower than the previously reported values for the effects of pazopanib on ATP binding or phosphorylation of MEK5 (FIGS. 4J-4K) by MAP3K2, which were higher than 500 nM) See Ahmad, et al., 2013, J. Biomol. Screen. 18:388.
Figure 4I:
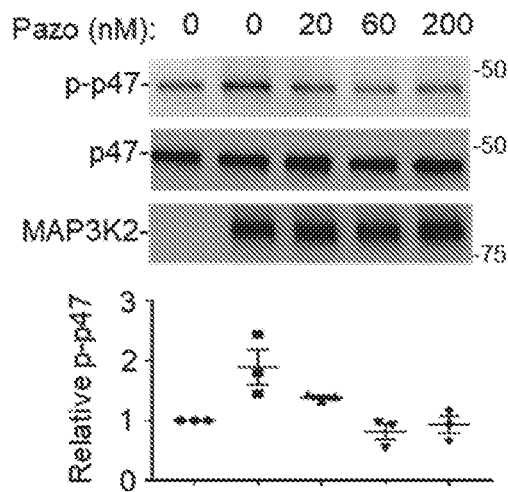
Figure 4J:
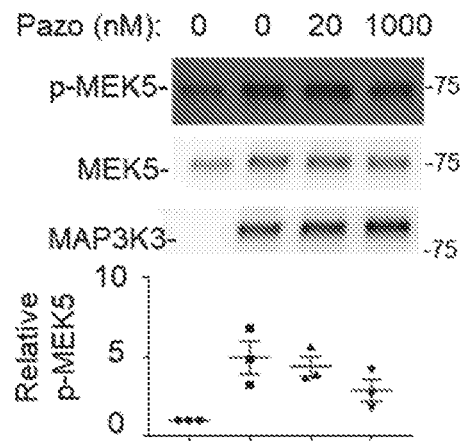
Figure 4K:
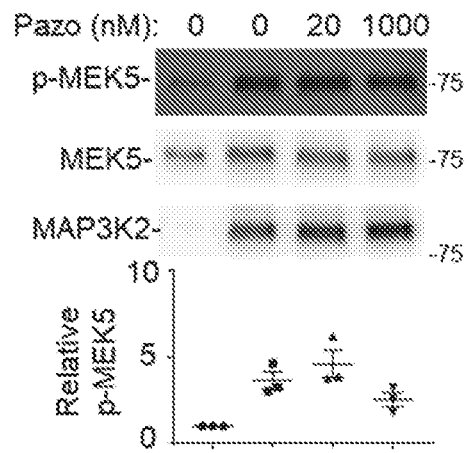

In vitro kinase assays were performed to determine the $IC_{50}$ for the inhibition of MEKK2 and 3 by pazopanib. Pazopanib inhibited MEKK3 with an $IC_{50}$ about 10 nM, whereas inhibiting MEKK2 with an $IC_{50}$ of 20 nM (FIGS. 4H-4I). These values are much lower than the $IC_{50}$ (>1 μM) for the only published MEKK2/3 substrate, MEK5 (FIGS. 4J-4K).

Example 5: Pazopanib Inhibits MAP3K2/3 and Reduces Lung Injury

Pazopanib is a FDA-approved drug for targeted cancer therapy. It inhibits a number of receptor tyrosine kinases including receptors for VEGF, FGF, PDGF and SCF (Keisner & Shah, 2011, Drugs 71:443-454). It also inhibits MAP3K2 with a potency comparable to its originally intended targets (Ahmad, et al., 2013, J. Biomol. Screen.

Figure 5A:
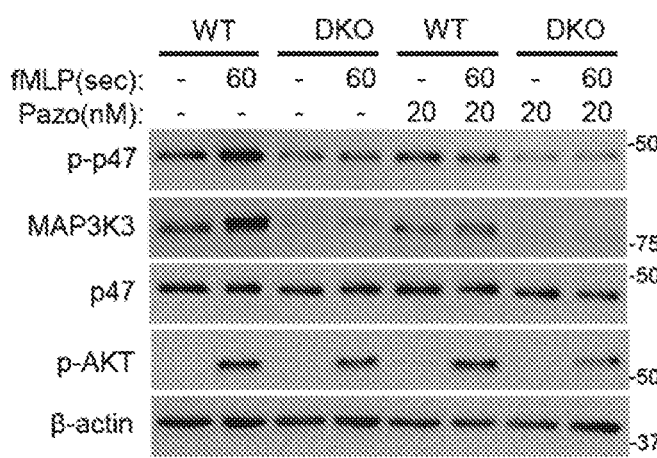
FIGS. 5A-5F illustrate the finding that pazopanib inhibits MAP3K2/3 and induces phenotypes similar to those of genetic MAP3K2/3 inactivation.
Figure 5B:
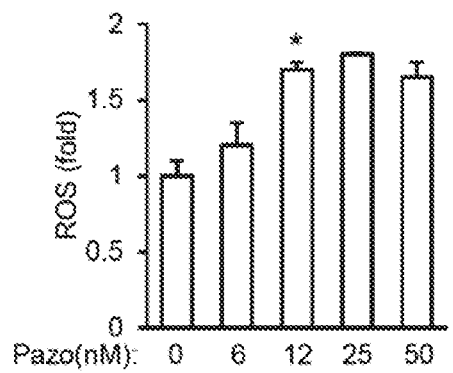
Figure 5C:
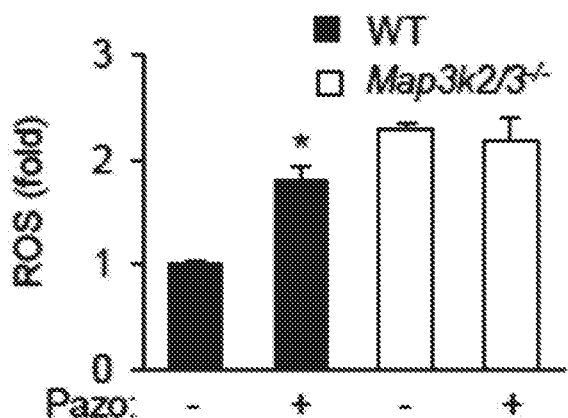
Figure 5D:
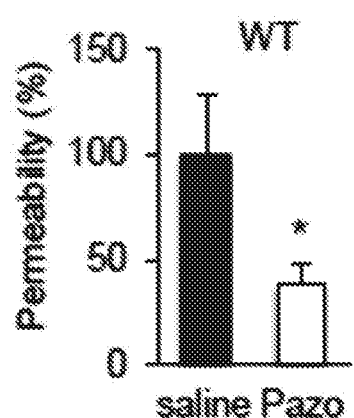
Figure 5E:
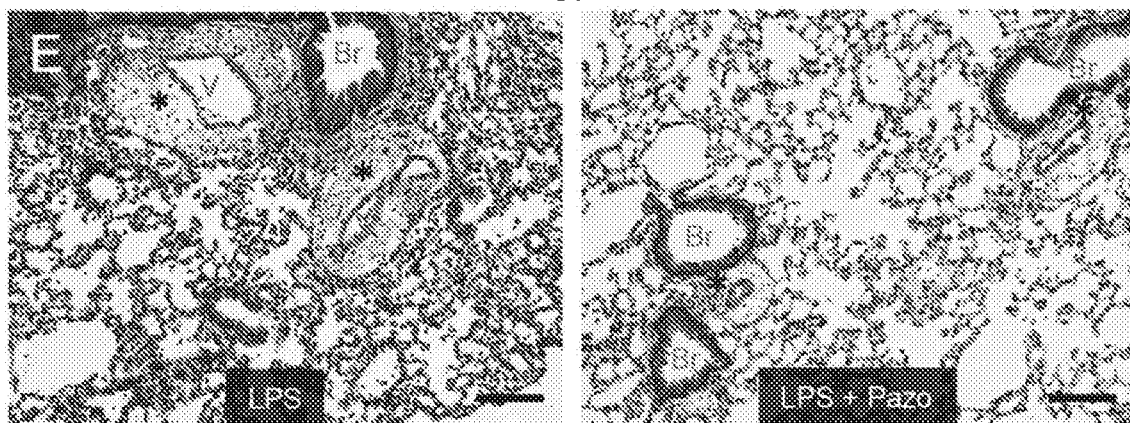
Figure 5F:
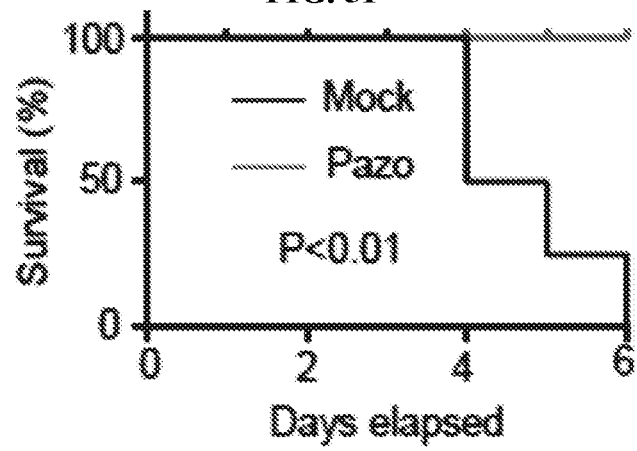

18:388-399). Pazopanib was tested in neutrophils and found to inhibit p47$^{phox}$ phosphorylation at Ser-208 detected by the phospho-specific antibody (FIG. 5A). Pazopanib also abrogated increase in MAP3K3 protein content induced by fMLP (FIG. 5A). Because MAP3K3 activates via autophosphorylation, this result is consistent with the idea that MAP3K3 stabilization may be a result of its activation and further confirms that pazopanib acts through MAP3Ks. Treatment of WT (FIG. 5B), but not MAP3K2/3-deficient (FIG. 5C), mouse neutrophils with pazopanib led to increases in the ROS production, indicating that pazopanib increases ROS production via MAP3K2/3. In addition, pazopanib increased ROS production from human neutrophils (FIGS. 12A-12B). The WT mice that were subjected to LPS-induced injury were fed with pazopanib. Similar to MAP3K2/3 HS-DKO, pazopanib treatment showed reduced pulmonary permeability (FIG. 5D), alveolar wall thickening, and edema (FIG. 5E). More importantly, pazopanib treatment reduced mortality in a prophylactic (FIG. 5F) or therapeutic (FIG. 12E) modality. For the prophylactic treatment, pazopanib was given two days before the lung injury, whereas the drug was given 24 hour after the injury.

Another model of acute lung injury induced by acid aspiration was used. Acid aspiration-induced ALI, also known as aspiration pneumonitis, results from pulmonary aspiration of the acid content of the stomach. This frequently occurs to patients with disturbed consciousness (e.g., drug overdose, seizures, cerebrovascular accident, sedation, anesthetic procedures) and is accounts up to 30% of all deaths associated with anesthesia. In this aspiration-induced ALI model, pazopanib treatment decreased pulmonary permeability (FIG. 12F), alveolar wall thickening, and edema (FIG. 12G). In addition, the treatment significantly extended the survival (FIG. 12H). Thus, these data together clearly demonstrate that pazopanib inhibit MAP3K2/3 and provide effective treatment in two different ALI models.

The preventative effect of pazopanib in the HCl model was also tested. Pazopanib was effective in reduction of permeability and extending survival (FIGS. 12I-12J).

Figure 17:
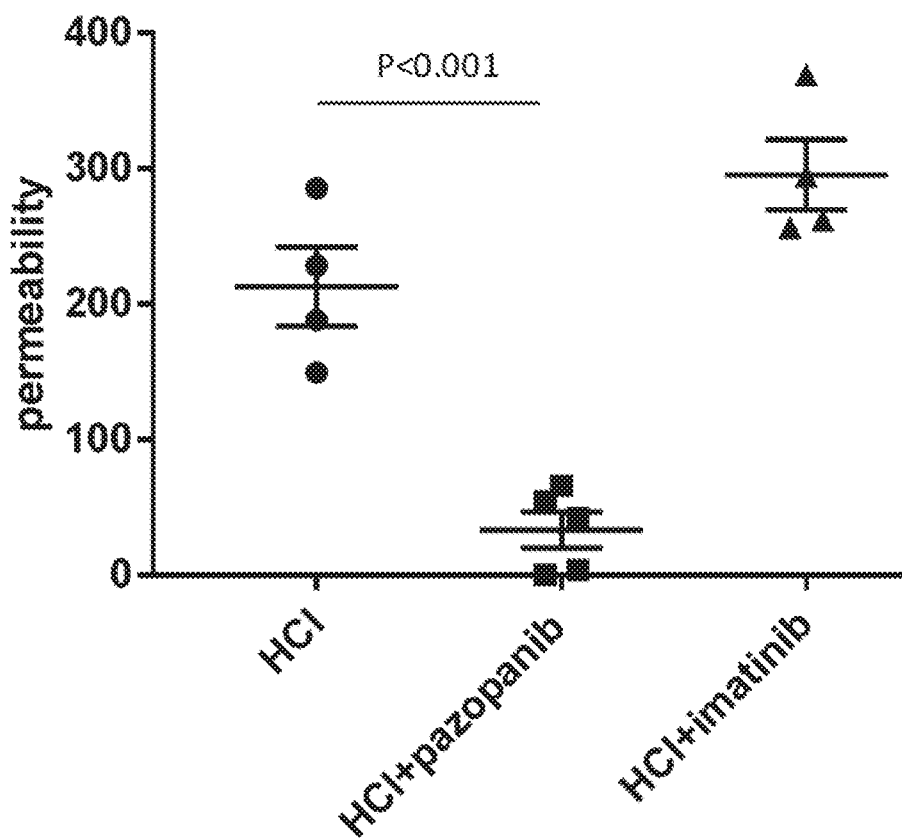
FIG. 17 is a graph illustrating the result that imatinib (4-[(4-methylpiperazin-1-yl)methyl]-N-(4-methyl-3-{[4-(pyridin-3-yl)pyrimidin-2-yl]amino}phenyl)benzamide, or GLEEVEC®) treatment does not attenuate HCl-induced lung injury. Mice (C57B1 female, 8 weeks) were treated with 1.5 mg/Kg Imatinib or pazopanib intra-nasally 1 h after lung injury induction by HCl. Six hours after lung injury induction, lung permeability (D) and histology (E) were examined. Data are presented as mean±sem (Student t-Test). Imatinib has a trend of aggravation of the injury.

Another tyrosine kinase inhibitor, imatinib, was also tested, and found to be ineffective in reducing lung permeability in the HCl-induced lung injury (FIG. 17). This result shows that the presently described beneficial effect of pazopanib is not shared by other tyrosine kinase inhibitors.

Example 6: Pazopanib Ameliorates Lung Injury Via MEKK2/3, p4'7, but not VEGFR

Figure 12D:
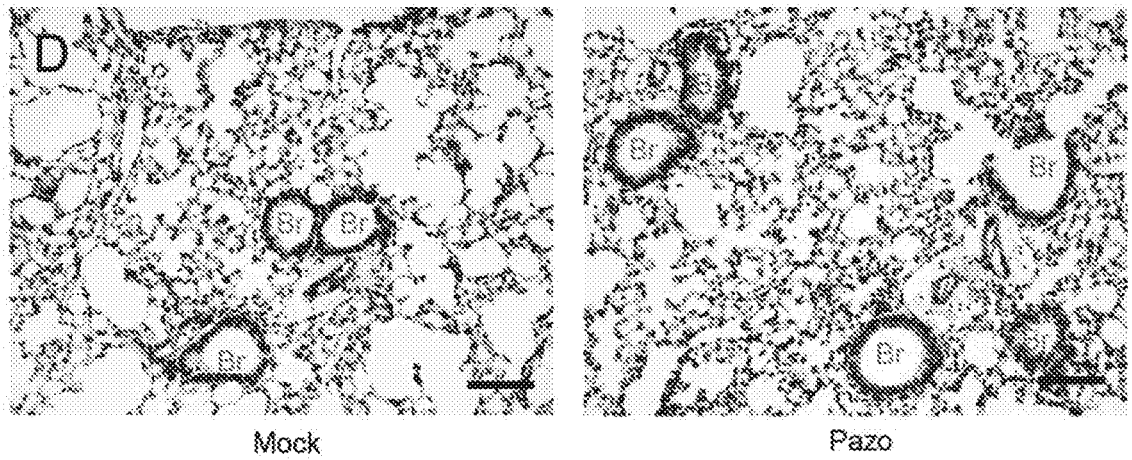
Figure 12E:
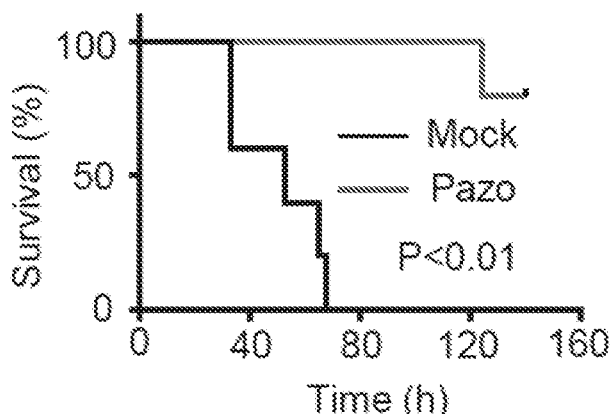
Figure 12F:
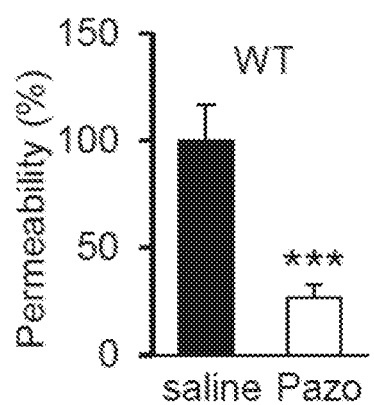
Figure 12G:
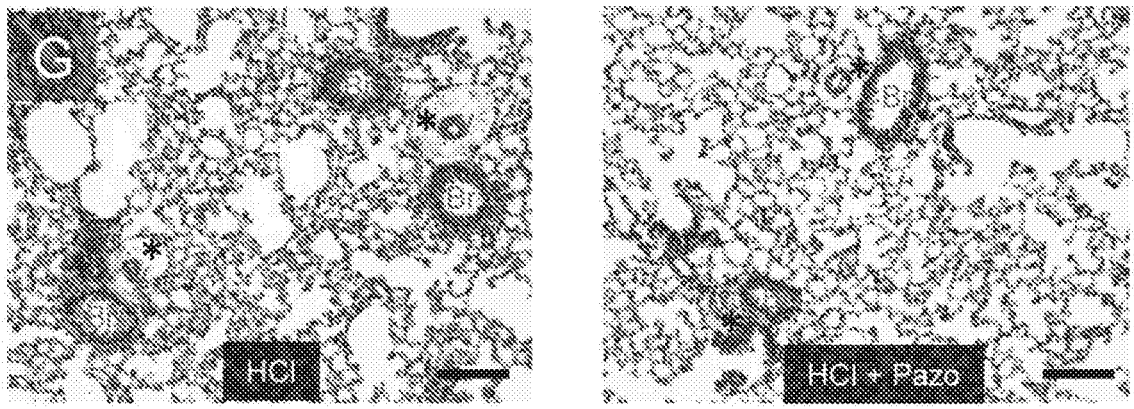
Figure 12H:
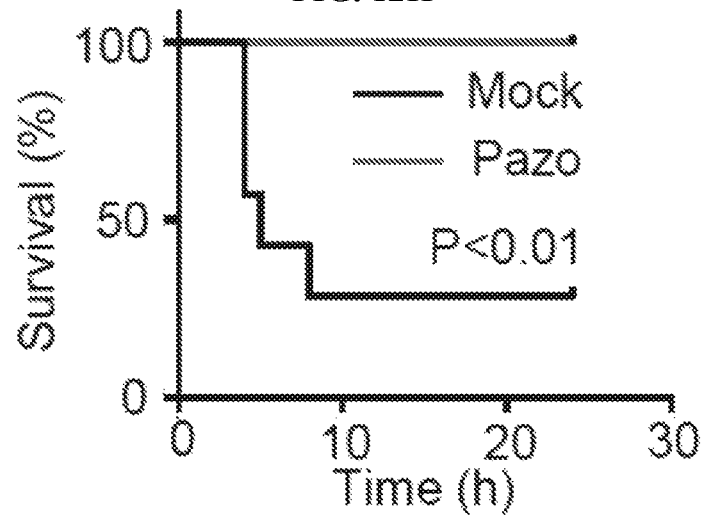
Figure 12I:
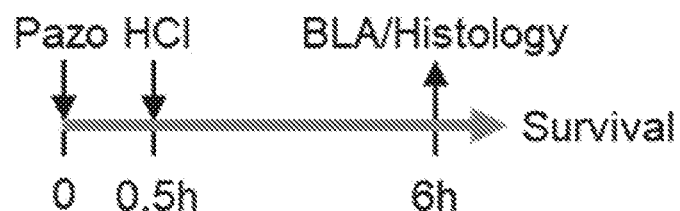
Figure 12J:
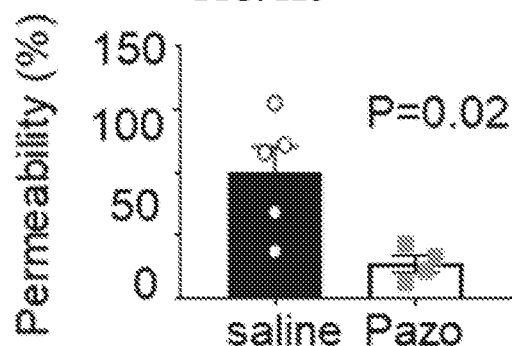
Figure 12K:
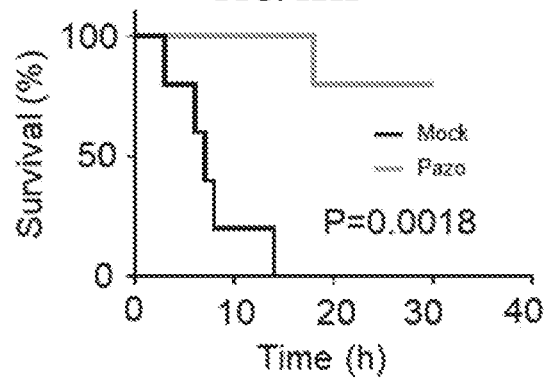
Figure 16A:
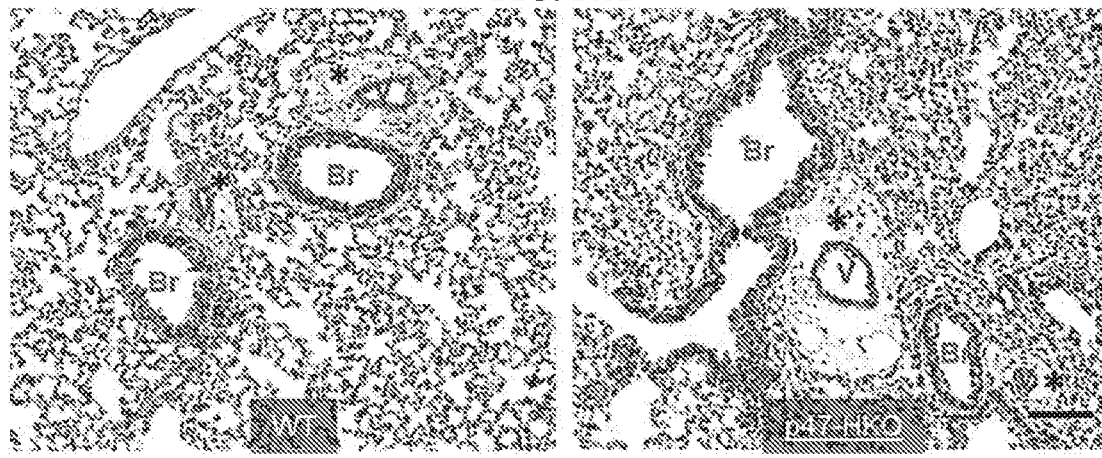
FIGS. 16A-16E illustrate the finding that pazopanib treatment attenuates HCl (FIGS. 16A-16C) or LPS-induced (FIGS. 16D-16E) lung injury in a therapeutic modality.
Figure 16B:
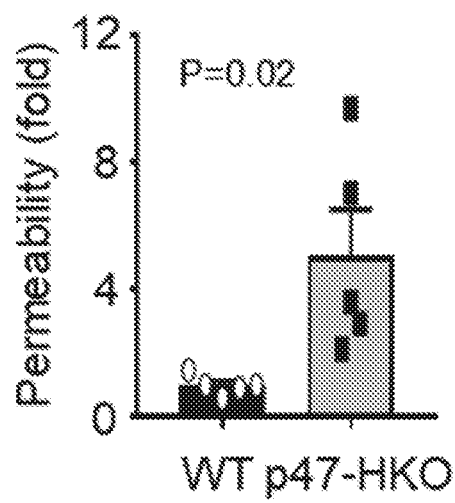
Figure 16C:
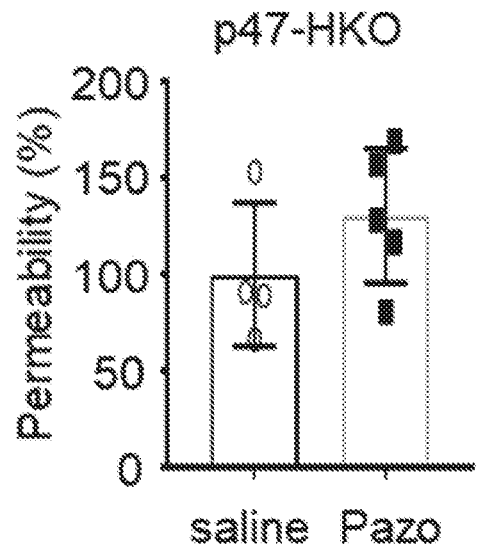
Figure 16D:
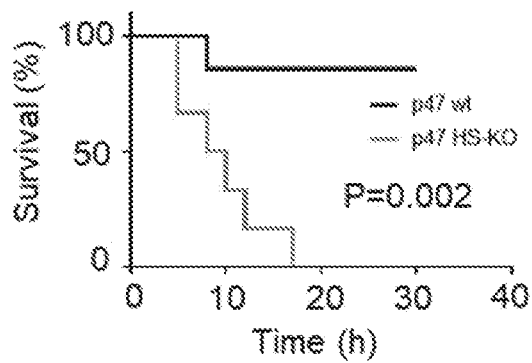
Figure 16E:
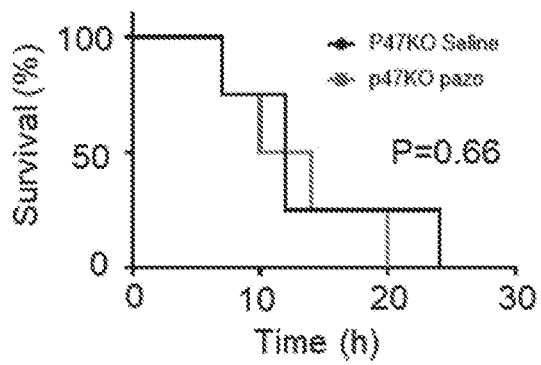

FIG. 12C-12D illustrates the finding that pazopanib ameliorates lung injury via MEKK2/3, as the drug had no effects on lung injury in mice lacking these kinases. In addition, pazopanib showed no effects in mice lacking p47$^{phox}$ (FIGS. 16C & 16E), the key subunit that produces ROS in neutrophils. The fact that mice lacking p47$^{phox}$ are more susceptible to the lung injury (FIGS. 16A-16B & 16D) is consistent with the finding that neutrophil ROS is protective in lung injury.

Figure 15:
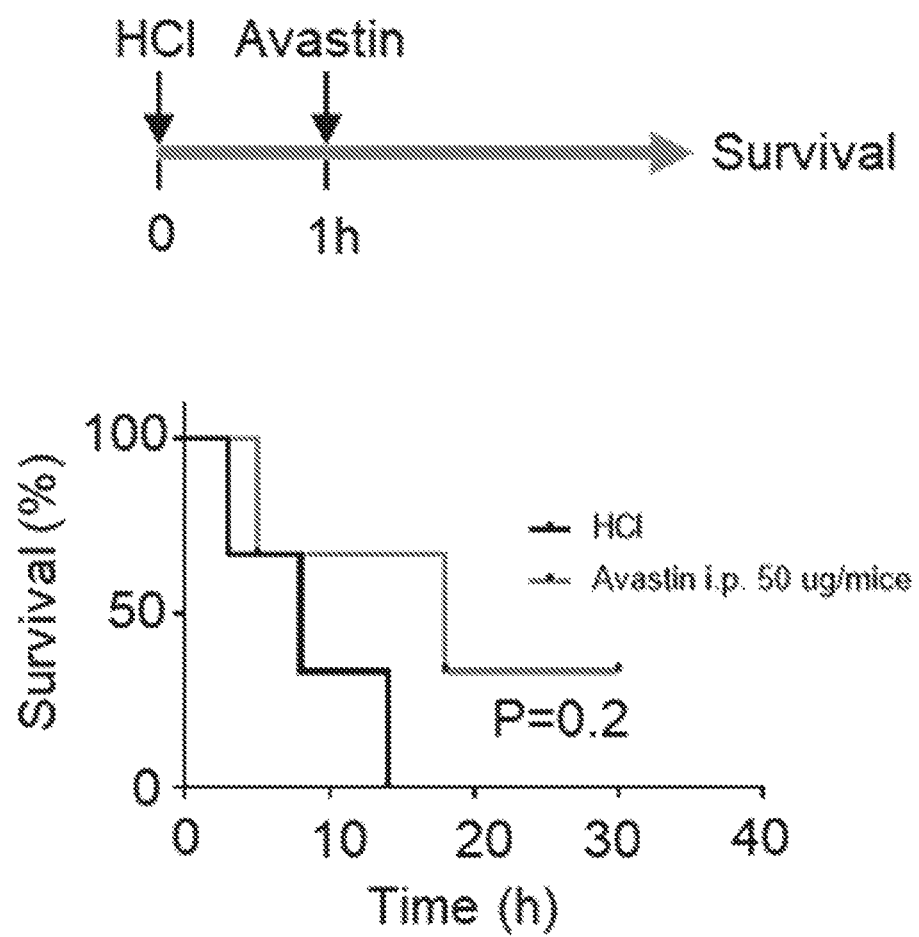
FIG. 15 illustrates the finding that Avastin, a VEGF inhibitor, has limited effects on HCl-induced acute lung injury.

Pazopanib also inhibits VEGFR. The effect of a neutralizing anti-VEGFR antibody was tested in the present model, and showed no effect in survival of mice subjected to lung injury (FIG. 15). Thus, pazopanib's inhibition of VEGFR does not play an important role in ameliorating lung injury.

Example 7: MAPK2/3 Inhibition Increases Lung AKT Activation

Figure 6:
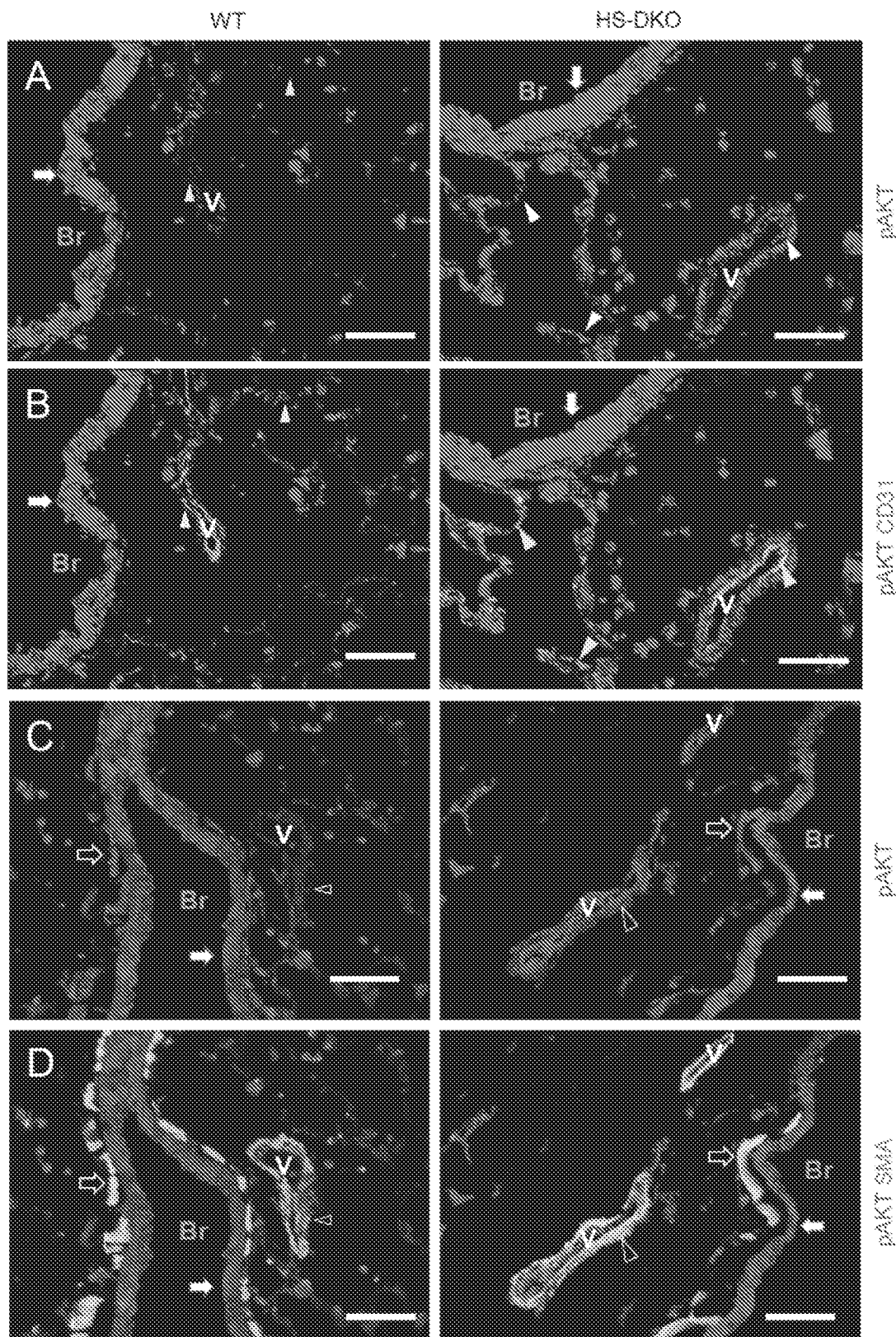
FIG. 6, comprising Panels A-D, illustrates the finding that AKT is hyperactivated in LPS-inured lungs of HS-DKO. Sections from LPS-inured lungs were stained for phospho-AKT and CD31 (Panels A-B) or smooth muscle actin (SMA; Panels C-D). Phospho-AKT staining is elevated in areas co-stained by CD31 (compare closed triangles) and SMA staining adjacent to blood vessels (V) (compared open triangles). By contrast, phospho-AKT staining at brachial walls (solid arrows) and brachial smooth muscle cells stained by SMA next to brachial wall (open arrows) remains the same between HS-DKO and WT samples. Images for CD31 and SMA staining alone are shown in FIGS. 13A-13F.
Figure 13A:
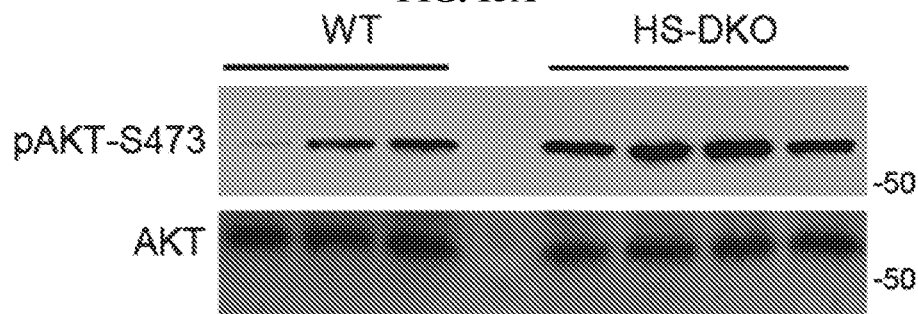
FIGS. 13A-13F illustrate hyperactivation of phospho-AKT by MAP3K2/3 inactivation.
Figure 13B:
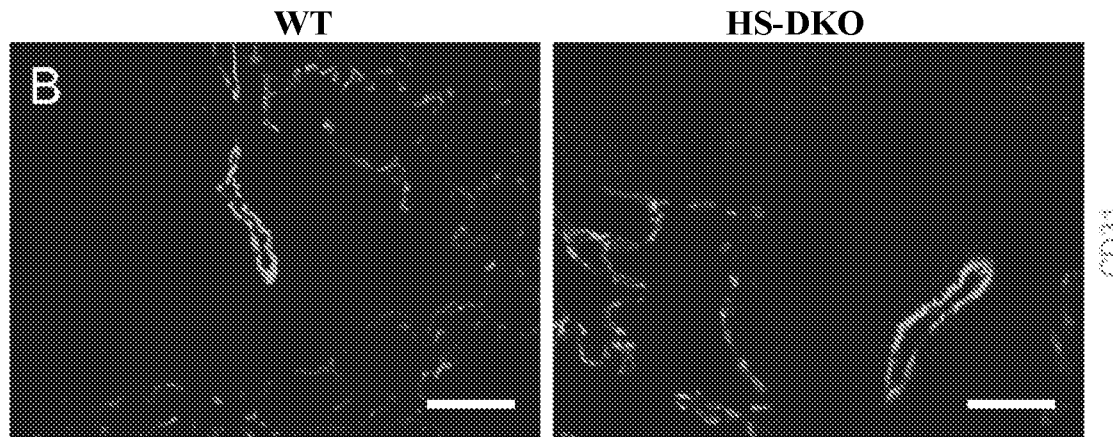
Figure 13C:
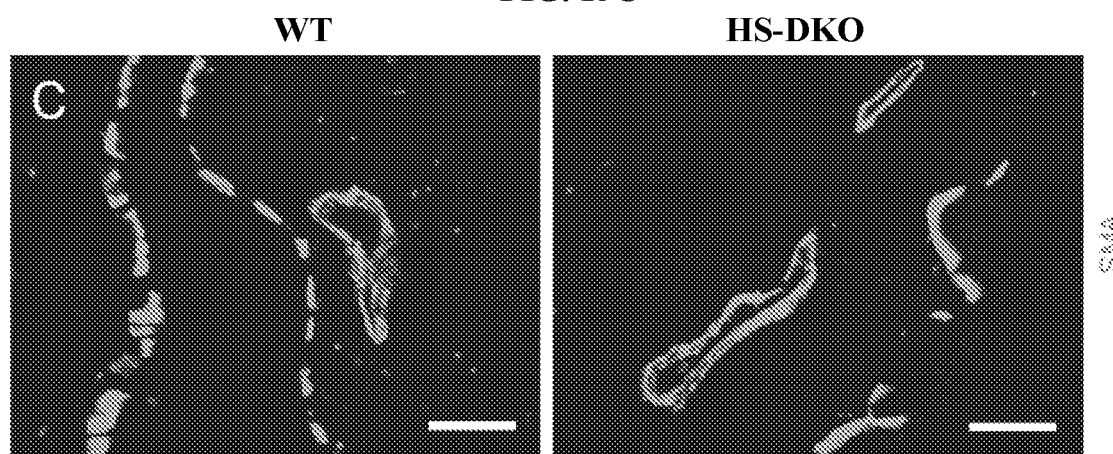
Figure 13D:
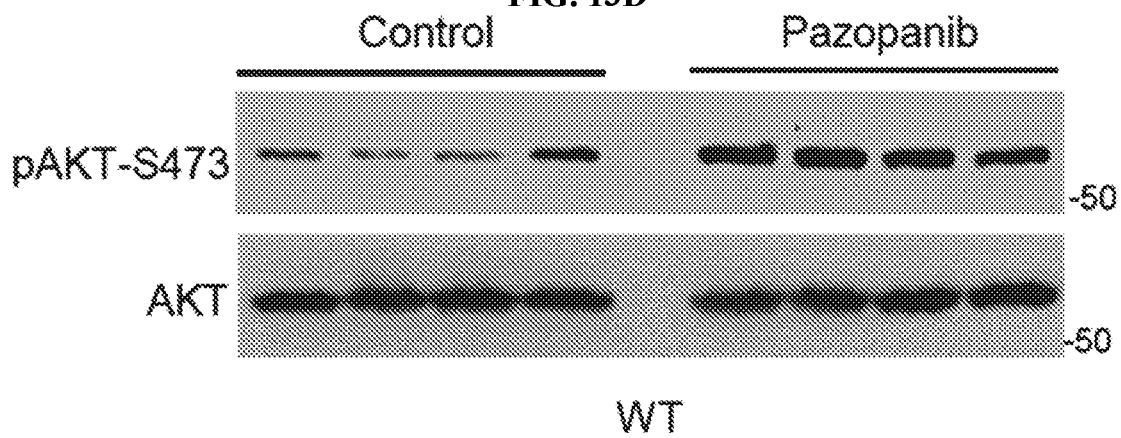
Figure 13E:
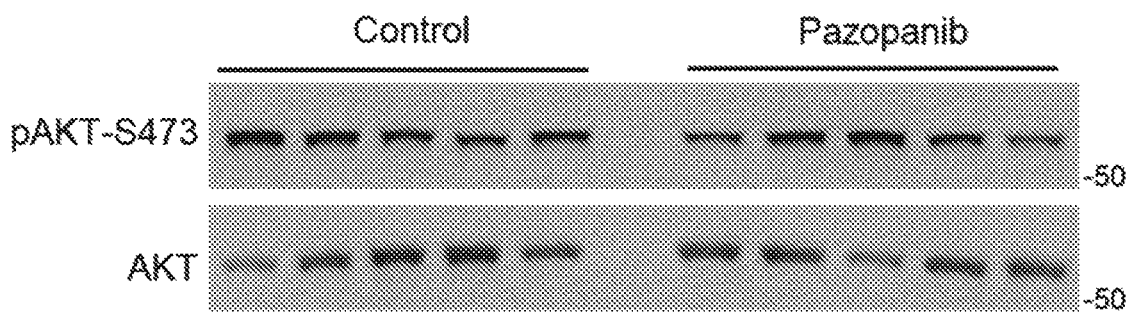
Figure 13F:
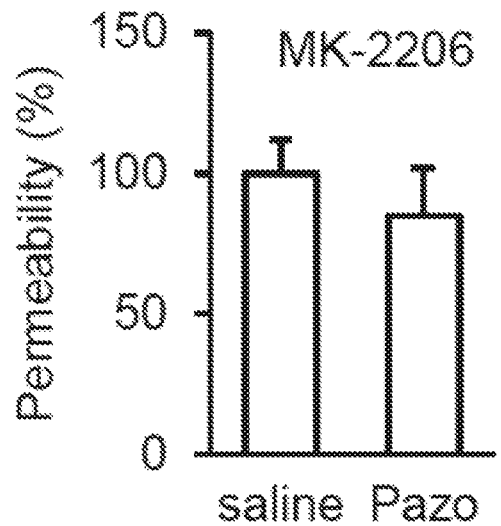
Figure 14A:
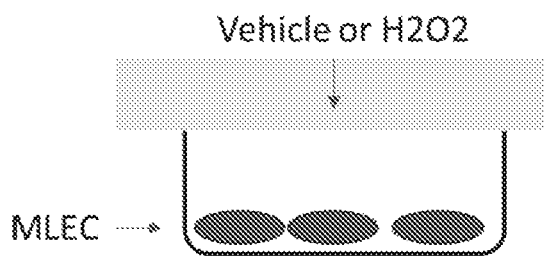
FIGS. 14A-14D illustrate activation of Rac1 by MAP3K2/3 inactivation.
Figure 14B:
Figure 14C:
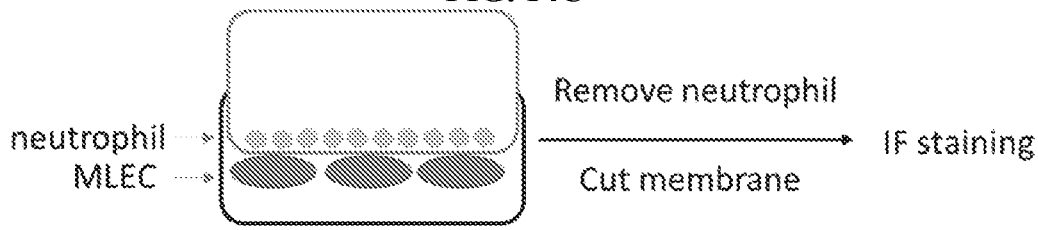
Figure 14D:
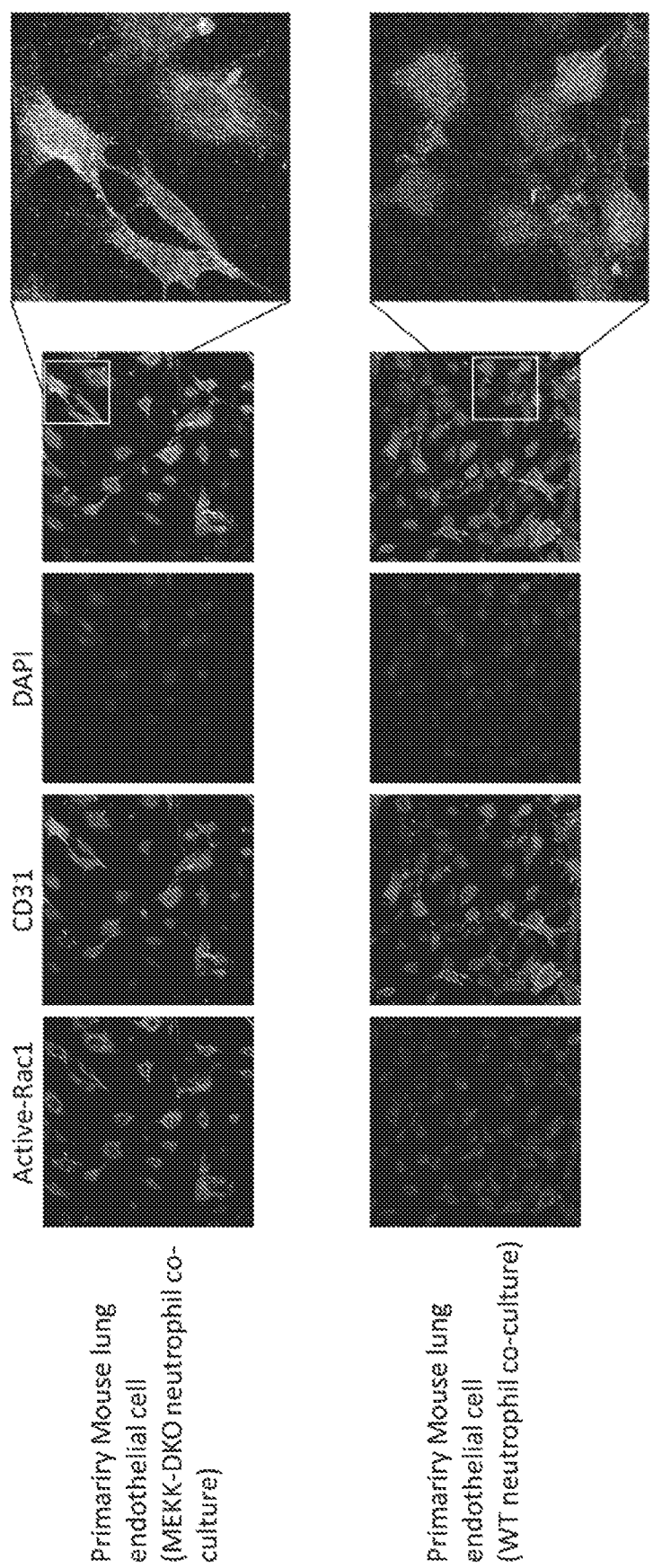

AKT signaling has a protective role in a murine model of ALI by preventing capillary leakage and clearing alveolar fluid. Moreover, ROS stimulates AKT activation in endothelial cells to strengthen vessel barrier integrity. AKT phosphorylation at Ser-473 was thus examined in LPS-treated lung samples, elevated AKT phosphorylation in the HS-DKO samples were found as compared to the controls (FIG. 13A). Because there was no difference in AKT phosphorylation between WT and DKO neutrophils (FIG. 5A), without wishing to be limited by any theory, the difference in AKT phosphorylation observed in the lung samples might be due to the differences in non-hematopoietic lung cells. Immunofluorescence of lung sections from LPS-treated mice showed higher levels of AKT phosphorylation in HS-DKO samples in pulmonary vessels and capillaries marked by CD31 staining (FIG. 6 (Panels A-B) & FIG. 13B) and vascular smooth muscle cells marked by smooth muscle actin staining (FIG. 6 (Panels C-D) & FIG. 13C). By contrast, the phospho-AKT staining of bronchial epithelial and smooth muscle cells was comparable between the WT and HS-DKO samples (FIG. 6 (Panels A-B) & FIGS. 13B-13C). In addition, pazopanib treatment recapitulates HS-DKO's effects on AKT phosphorylation; the inhibitor increased AKT phosphorylation in LPS-injured lungs (FIG. 13D). This effect of pazopanib depends on the presence of MAP3K2 and 3, as the inhibitor had little effect on AKT phosphorylation in the HS-DKO lungs (FIG. 13E). Furthermore, treatment of the mice with the AKT inhibitor MK-2206 (8-[4-(1-Aminocyclobutyl)phenyl]-9-phenyl-2H-[1,2,4]triazolo[3,4-f][1,6]naphthyridin-3-one) abrogated the effect of pazopanib on permeability (FIG. 13F).

Figure 7A:
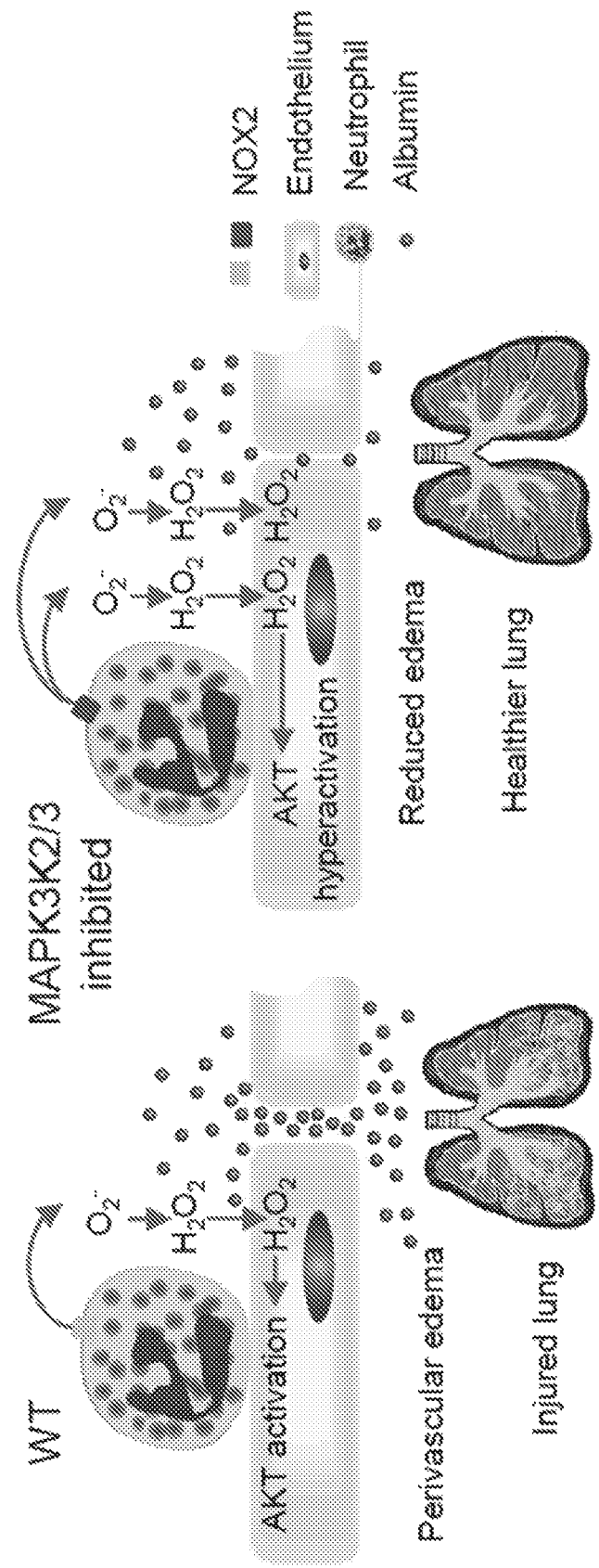
FIGS. 7A-7D illustrate the finding that neutrophil lacking MAP3K2/3 increase AKT activation in endothelial cells via $H_2O_2$.
Figure 7B:
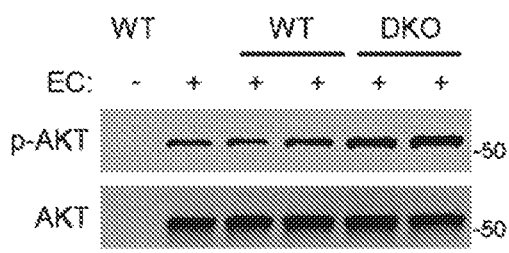
Figure 7C:
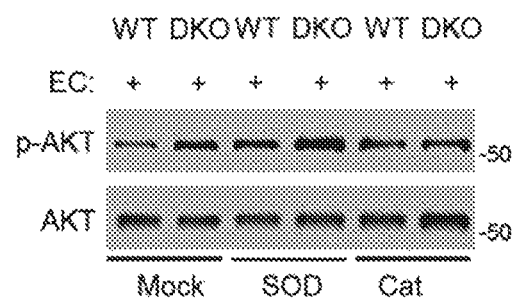
Figure 7D:
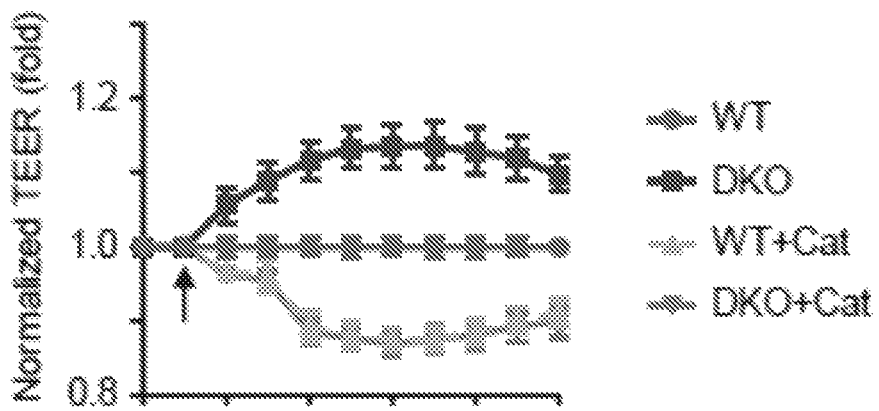

The aforementioned data, together with the knowledge that ROS can stimulate AKT phosphorylation in endothelial cells, support a non-limiting model (FIG. 7A) to suggest that, during acute lung injury, MAP3K2/3-deficient neutrophils release more ROS, which augments AKT activation in endothelial cells and vascular smooth muscle cells, leading to improved vascular integrity and reduced permeability. To further test this non-limiting hypothesis, co-culture of WT and DKO neutrophils was performed with mouse lung endothelial cells. Mouse endothelial cells co-cultured with fMLP-activated DKO neutrophils had elevated phospho-AKT compared to co-culture with activated WT neutrophils (FIG. 7B). This phospho-AKT elevation could be abrogated by the presence of catalase, but not superoxidase dismutase (SOD) (FIG. 7C). Catalase catalyzes the conversion of $H_2O_2$ to water, whereas SOD converts superoxide to $H_2O_2$. Moreover, co-culture of activated DKO neutrophils with mouse endothelial cells increased trans-endothelial electrical resistance (PEER) over that of activated WT neutrophils, and this difference in TEER could also be abrogated by the addition of catalase (FIG. 7D). Thus, these results together support the conclusion that activated DKO neutrophils can elevate phospho-AKT and improve endothelial junction integrity in co-cultured endothelial cells via $H_2O_2$ and is consistent with the non-limiting model described in FIG. 7A.

Knowing that AKT may regulate endothelial junction integrity via activation of RAC1 small GTPase, it was tested if $H_2O_2$ can activate RAC in mouse endothelial cells. Indeed, $H_2O_2$ was found to activate RAC1 in the endothelial cell. In addition, co-culture of neutrophils lacking MEKK2/3 led to greater RAC1 activation than WT neutrophils, suggesting MEKK2/3 KO neutrophils can cause hyperactivation of RAC1 in endothelial cells. These findings are consistent with the hypothesis depicted in FIG. 7A.

Figure 18:
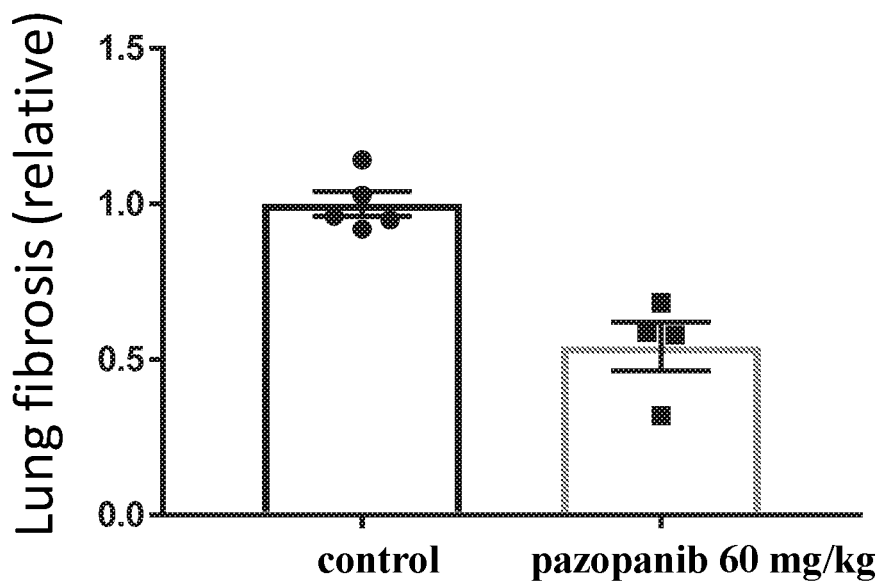
FIG. 18 is a bar graph illustrating the result that pazopanib inhibits bleomycin-induced lung fibrosis. Mice (C57B1 female, 8 weeks) were treated with 0.05 unit bleomycin once. One week later, the mice were given orally 60 mg/kg pazopanib for five days, and the lung fibrosis was determined by measuring the levels of hydroxyproline.

A long detrimental effect of ALI is fibrosis. It was thus tested if pazopanib can inhibit lung fibrosis. A bleomycin-induced lung fibrosis model was used in this study: Gan, et al., 2012, Nat. Cell Biol. 14:686. Pazopanib was found to inhibit lung fibrosis (FIG. 18), suggesting that the mechanisms of action of pazopanib in curbing ALI are multifaceted.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or ameliorating acute lung injury (ALI) or lung fibrosis in a subject, the method comprising administering to the subject a therapeutically effective amount of pazopanib, or a salt or solvate thereof,
    using an administration route selected from the group consisting of oral, parenteral, nasal, inhalational, intratracheal, intrapulmonary, and intrabronchial;
    wherein the pazopanib, or a salt or solvate thereof, is the only therapeutic agent administered to the subject to treat or ameliorate the ALI or lung fibrosis.

2. The method of claim 1, wherein the administration is done using a nebulizer.

3. The method of claim 1, wherein the subject is in an intensive care unit (ICU) or emergency room (ER).

4. The method of claim 1, wherein the acute lung injury is acute respiratory distress syndrome (ARDS).

5. The method of claim 1, wherein the subject is further subjected to low tidal volume ventilation.

6. The method of claim 1, wherein the-administration route is intravenous.

7. The method of claim 1, wherein the pazopanib, or a salt or solvate thereof, is administered to the subject at a frequency selected from the group consisting of about three times a day, about twice a day, about once a day, about every other day, about every third day, about every fourth day, about every fifth day, about every sixth day and about once a week.

8. The method of claim 1, wherein the pazopanib, or a salt or solvate thereof, is formulated as a dry powder blend.

9. The method of claim 1, wherein administration of the pazopanib, or a salt or solvate thereof, to the subject does not cause at least one significant adverse reaction, side effect or toxicity associated with oral/systemic administration of the pazopanib, or a salt or solvate thereof, to a subject suffering from cancer.

10. The method of claim 9, wherein the at least one adverse reaction, side effect or toxicity is selected from the group consisting of hepatotoxicity, prolonged QT intervals and torsades de pointes, hemorrhagic event, decrease or hampering of coagulation, arterial thrombotic event, gastrointestinal perforation or fistula, hypertension, hypothyroidism, proteinuria, diarrhea, hair color changes, nausea, anorexia, and vomiting.

11. The method of claim 1, wherein the subject is dosed with an amount of pazopanib, or a salt or solvate thereof, that is lower than the amount of pazopanib, or a salt or solvate thereof, with which a subject suffering from cancer is dosed orally/systemically for cancer treatment.

12. The method of claim 1, wherein the subject is a mammal.

13. The method of claim 12, wherein the mammal is a human.

14. A kit comprising pazopanib, or a salt or solvate thereof, an applicator, and an instructional material for use thereof, wherein the instructional material comprises instructions for treating or ameliorating acute lung injury or lung fibrosis in a subject, wherein the pazopanib, or a salt or solvate thereof, is the only therapeutic agent to be administered to the subject to treat or ameliorate the ALI or lung fibrosis, using an administration route selected from the group consisting of nasal, inhalational, intratracheal, intrapulmonary, and intrabronchial.

15. The kit of claim 14, wherein the pazopanib, or a salt or solvate thereof, is formulated as a dry powder blend.

* * * * *